United States Patent
Ribble

(10) Patent No.: US 9,152,768 B2
(45) Date of Patent: Oct. 6, 2015

(54) METHOD AND SYSTEM FOR PATIENT CARE MANAGEMENT

(75) Inventor: David Ribble, Indianapolis, IN (US)

(73) Assignee: Hill-Rom Services, Inc., Batesville, IN (US)

(*) Notice: Subject to any disclaimer, the term of this patent is extended or adjusted under 35 U.S.C. 154(b) by 1010 days.

(21) Appl. No.: 13/245,378

(22) Filed: Sep. 26, 2011

(65) Prior Publication Data

US 2013/0074852 A1    Mar. 28, 2013

(51) Int. Cl.

| G06F 19/00 | (2011.01) |
|---|---|
| G06F 3/00 | (2006.01) |
| H04W 4/00 | (2009.01) |
| H04M 19/04 | (2006.01) |
| A61B 5/00 | (2006.01) |
| A61B 5/11 | (2006.01) |

(52) U.S. Cl.
CPC .......... *G06F 19/3481* (2013.01); *G06F 19/345* (2013.01); *A61B 5/1103* (2013.01); *A61B 5/4815* (2013.01)

(58) Field of Classification Search
USPC .......... 340/575, 576; 600/301, 509, 544, 595
See application file for complete search history.

(56) References Cited

U.S. PATENT DOCUMENTS

| 4,815,657 A * | 3/1989 | Tsukuda ........................ 236/47 |
|---|---|---|
| 4,836,219 A * | 6/1989 | Hobson et al. ............... 600/595 |
| 4,908,878 A * | 3/1990 | Tarragano ........................ 2/15 |
| 4,928,090 A * | 5/1990 | Yoshimi et al. .............. 340/575 |
| 5,195,606 A | 3/1993 | Martyniuk |
| 5,280,791 A * | 1/1994 | Lavie ............................. 600/509 |
| 5,479,939 A * | 1/1996 | Ogino ........................... 600/595 |
| 6,014,346 A | 1/2000 | Malone |
| 7,041,049 B1 | 5/2006 | Raniere |
| 7,524,279 B2 | 4/2009 | Auphan |
| 7,956,755 B2 * | 6/2011 | Lee et al. ...................... 340/575 |
| 8,073,535 B2 * | 12/2011 | Jung et al. .................... 600/547 |
| 2003/0095476 A1 * | 5/2003 | Mollicone et al. ............ 368/250 |
| 2005/0084075 A1 * | 4/2005 | Kotzin ............................ 379/38 |
| 2005/0249023 A1 * | 11/2005 | Bodlaender ................... 365/232 |
| 2008/0021344 A1 * | 1/2008 | Jung et al. .................... 600/549 |
| 2008/0071150 A1 * | 3/2008 | Miesel et al. ................. 600/301 |
| 2009/0264715 A1 | 10/2009 | Auphan |
| 2009/0265236 A1 * | 10/2009 | Schultz et al. ................. 705/14 |
| 2009/0265764 A1 * | 10/2009 | Schultz et al. .................. 726/4 |

(Continued)

OTHER PUBLICATIONS

EP Partial Search Report for EP12185180; Place of Search—Munich; Date of Completion of Search—Mar. 5, 2013.

*Primary Examiner* — Fekadeselassie Girma
(74) *Attorney, Agent, or Firm* — Barnes & Thornburg LLP

(57) ABSTRACT

A method for governing care of a person includes determining the importance of a candidate activity (84) relative to the importance of patient sleep continuity (104) and, if the candidate activity is more important than sleep continuity, carrying out the activity or indicating the acceptability of carrying out the activity (106) and, if the candidate activity is not more important than sleep continuity, refraining from carrying out the activity or indicating the unacceptability of carrying out the activity (108). A system for patient care governance comprises a decision engine (80) for determining the importance of the candidate activity relative to the importance of sleep continuity, and a controller (92) responsive to the decision engine for issuing a command to carry out the activity or indicate the acceptability of carrying out the activity (106), refrain from carrying out the activity or indicate the unacceptability of carrying out the activity (108).

26 Claims, 20 Drawing Sheets

(56) References Cited

U.S. PATENT DOCUMENTS

| | | | |
|---|---|---|---|
| 2011/0034811 A1* | 2/2011 | Naujokat et al. | 600/484 |
| 2011/0224510 A1 | 9/2011 | Oakhill | |
| 2011/0230790 A1 | 9/2011 | Kozlov | |
| 2012/0139722 A1* | 6/2012 | Wong et al. | 340/539.12 |
| 2012/0238800 A1* | 9/2012 | Naujokat et al. | 600/26 |

* cited by examiner

| 1 | 2 | 3 | 4 | 5 | 6 | 7 | 8 | 9 | 10 | 11 |
|---|---|---|---|---|---|---|---|---|---|---|
| Cycle | Stage | Duration Dependent Sleep Value 0=Low 5=High | Duration Independent Sleep Value 1=lowest 3=highest | Desired Duration (minutes) | Achieved? | Duration Dependent Sleep Score | Duration Independent Sleep Score | Cummulative Sleep Score | Unadjusted Sleep Threshold | Threshold |
| 1 | 1 | 0 | 1 |  | N/A | 0 | 1 | 1 | 60 | 45 |
| 1 | 2 | 0 | 1 |  | N/A | 0 | 1 | 2 | 60 | 45 |
| 1 | 3 | 3 | 1 | 25 | yes | 3 | 1 | 6 | 60 | 45 |
| 1 | 4 | 4 | 1 | 10 | no | 0 | 1 | 7 | 60 | 45 |
| 1 | REM1 | 5 | 2 | 7 | yes | 5 | 2 | 14 | 60 | 45 |
| 1 | REM2 | 4 | 2 | 12 | yes | 4 | 2 | 20 | 60 | 45 |
| 1 | REM3 | 3 | 3 | 20 | yes | 3 | 3 | 26 | 60 | 45 |
| 1 | REM4 | 2 | 2 | 25 | yes | 2 | 2 | 30 | 60 | 45 |
| 1 | Balance of REM | 1 | 1 | unspcfd. | yes | 1 | 1 | 32 | 60 | 45 |
| 2 | 1 | 0 | 1 |  | N/A | 0 | 1 | 33 | 60 | 45 |
| 2 | 2 | 0 | 1 |  | N/A | 0 | 1 | 34 | 60 | 45 |
| 2 | 3 | 3 | 1 | 25 | yes | 3 | 1 | 38 | 60 | 45 |
| 2 | 4 | 4 | 1 | 10 | yes | 4 | 1 | 43 | 60 | 45 |
| 2 | REM1 | 5 | 2 | 7 | yes | 5 | 2 | 50 | 60 | 45 |
| 2 | REM2 | 4 | 2 | 12 | no | 0 | 1 | 51 | 60 | 45 |
| 2 | REM3 | 3 | 3 | 20 | yes | 3 | 3 | 57 | 60 | 45 |
| 2 | REM4 | 2 | 2 | 25 |  |  |  |  | 60 | 45 |
| 2 | Balance of REM | 1 | 1 | unspcfd. |  |  |  |  | 60 | 45 |
| 3 | 1 | 0 |  |  |  |  |  |  | 60 | 45 |
| 3 | 2 | 0 |  |  |  |  |  |  | 60 | 45 |
| 3 | 3 | 3 |  | 25 |  |  |  |  | 60 | 45 |
| 3 | 4 | 4 |  | 10 |  |  |  |  | 60 | 45 |
| 3 | REM1 | 5 |  | 7 |  |  |  |  | 60 | 45 |
| 3 | REM2 | 4 |  | 12 |  |  |  |  | 60 | 45 |
| 3 | REM3 | 3 |  | 20 |  |  |  |  | 60 | 45 |
| 3 | REM4 | 2 |  | 25 |  |  |  |  | 60 | 45 |
| 3 | Balance of REM | 1 |  | unspcfd. |  |  |  |  | 60 | 45 |

FIG. 11A

| 1 | 2 | 3 | 4 | 5 | 6 | 7 | 8 | 9 | 10 | 11 |
|---|---|---|---|---|---|---|---|---|---|---|
| Cycle | Stage | Duration Dependent Sleep Value 0=Low 5=High | Duration Independent Sleep Value 1=lowest 3=highest | Desired Duration (minutes) | Achieved? | Duration Dependent Sleep Score | Duration Independent Sleep Score | Cummulative Sleep Score | Unadjusted Sleep Threshold | Threshold |
| 4 | 1 | 0 | | | | | | | 60 | 45 |
| 4 | 2 | 0 | | | | | | | 60 | 45 |
| 4 | 3 | 3 | | 25 | | | | | 60 | 45 |
| 4 | 4 | 4 | | 10 | | | | | 60 | 45 |
| 4 | REM1 | 5 | | 7 | | | | | 60 | 45 |
| 4 | REM2 | 4 | | 12 | | | | | 60 | 45 |
| 4 | REM3 | 3 | | 20 | | | | | 60 | 45 |
| 4 | REM4 | 2 | | 25 | | | | | 60 | 45 |
| 4 | Balance of REM | 1 | | unspcfd. | | | | | 60 | 45 |

FIG. 11B

Ration of Care Activity Importance to Sleep Distruption Potential

| A | B | C | D |
|---|---|---|---|
| Candidate Activity | Importance 5 = High 1 = Low | Sleep Disruptive Potential | Ratio Importance to Disruptive Potential |
| MCM to Keep Skin < 98° | 5 | 3 High/Certain | 1.7 |
| MCM to Keep Skin < 96° | 4 | 2 Medium | 2.0 |
| SCD Const. | 5 | 0 None | >3.0 |
| SCD Low/Slow | 3 | 1 Low | 3.0 |
| SCD High/Fast | 2 | 3 | 0.67 |
| CLRT | 2 | 3 | 0.67 |
| Percussion | 2 | 3 | 0.67 |
| Pain Assessment | 2 | 3 | 0.67 |
| Skin Assessment | 2 | 3 | 0.67 |
| Turn Patient Manually | 1 | 3 | 0.33 |
| Bathe Patient | 1 | 3 | 0.33 |
| Toilet | 5 | 1 | 5.0 |
| Med A | 5 | 3 | 1.67 |
| Med B | 4 | 3 | 1.33 |
| Med C | 3 | 3 | 1.0 |
| Med D | 2 | 3 | 0.67 |
| Maintenance/Housekeeping | 0 | 2 | 0 |
| Phone Call Enabled | 0 | 2 | 0 |
| "Quiet Please" Sign Off | 0 | 2 | 0 |
| Speaker Activation | 1 | 2 | 0.5 |
| Lights | 1 | 2 | 0.5 |

FIG. 13

| 1 | 2 | 3 | 4 | 5 | 6 | 7 | 8 | 9 | 10 | 11 | 12 | 13 |
|---|---|---|---|---|---|---|---|---|---|---|---|---|
| Cycle | Stage | Duration Dependent Sleep Value 0=Low 5=High | Duration Independent Sleep Value 1=lowest 3=highest | Desired Duration (minutes) | | Duration Dependent Sleep Score | Duration Independent Sleep Score | Cum-mulative Sleep Score | Max. Attainable Sleep Score | Fraction of Max. Attained | Unadjusted "Disturb After Sleep Threshold | Acceptable to "Disturb for Candidate Activity? |
| 1 | 1 | 0 | 1 | | | 0 | 1 | 1 | 1 | 1.00 | 0.60 | Yes |
| 1 | 2 | 0 | 1 | | | 0 | 1 | 2 | 2 | 1.00 | 0.70 | Yes |
| 1 | 3 | 3 | 1 | 25 | | 3 | 1 | 6 | 6 | 1.00 | 0.80 | Yes |
| 1 | 4 | 4 | 1 | 10 | | 0 | 1 | 7 | 11 | 0.64 | 0.85 | No |
| 1 | REM1 | 5 | 2 | 7 | | 5 | 2 | 14 | 18 | 0.78 | 0.85 | No |
| 1 | REM2 | 4 | 2 | 12 | | 4 | 2 | 20 | 24 | 0.83 | 0.85 | No |
| 1 | REM3 | 3 | 3 | 20 | | 3 | 3 | 26 | 30 | 0.87 | 0.95 | No |
| 1 | REM4 | 2 | 2 | 25 | | 2 | 2 | 30 | 34 | 0.88 | 0.95 | No |
| 1 | Balance of REM | 1 | 1 | unspcfd. | | 1 | 1 | 32 | 36 | 0.89 | 0.95 | No |
| 2 | 1 | 0 | 1 | | | 0 | 1 | 33 | 37 | 0.89 | 0.95 | No |
| 2 | 2 | 0 | 1 | | | 0 | 1 | 34 | 38 | 0.89 | 0.95 | No |
| 2 | 3 | 3 | 1 | 25 | | 3 | 1 | 38 | 42 | 0.90 | 0.95 | No |
| 2 | 4 | 4 | 1 | 10 | | 4 | 1 | 43 | 47 | 0.91 | 0.90 | Yes |
| 2 | REM1 | 5 | 2 | 7 | | 5 | 2 | 50 | 54 | 0.93 | 0.90 | Yes |
| 1 | REM2 | 4 | 2 | 12 | | 0 | 1 | 52 | 60 | 0.87 | 0.90 | No |
| 2 | REM3 | 3 | 3 | 20 | | 3 | 3 | 58 | 66 | 0.88 | 0.90 | No |
| 2 | REM4 | 2 | 2 | 25 | | | | | 70 | | | |
| 2 | Balance of REM | 1 | 1 | unspcfd. | | | | | 72 | | | |

FIG. 17

METHOD AND SYSTEM FOR PATIENT CARE MANAGEMENT

TECHNICAL FIELD

The subject matter described herein relates to a method and system for governing the care of a patient. One example application for the method and system is managing the sleep of a hospital patient with due consideration for the relative value of sleep and of the sleep disruptive potential and benefits of a candidate activity.

BACKGROUND

A patient in a hospital or other health care setting requires the restorative benefits of sleep. However it is also necessary to carry out patient care activities, to control the environment in the patient's room or care space, and to attend to housekeeping and maintenance tasks in the patient's room or care space. At least some of these activities, or the consequences of them, can disrupt the patient's sleep. For any given activity it will be beneficial to assess the benefits of patient sleep relative to the sleep disruptive potential and/or benefit of carrying out the activity and, on the basis of that assessment, judge the advisability of carrying out the activity.

SUMMARY

A method for governing care of a person comprises determining the importance of a candidate activity relative to the importance of patient sleep continuity and, if the candidate activity is more important than sleep continuity, carrying out the activity or indicating the acceptability of carrying out the activity, and if the candidate activity is not more important than sleep continuity, refraining from carrying out the activity or indicating that the unacceptability of carrying out the activity. A system for patient care governance comprises a decision engine for determining the importance of a candidate activity relative to the importance of sleep continuity and a controller responsive to the decision engine for issuing a command to carry out the activity or to indicate the acceptability of carrying out the activity or to refrain from carrying out the activity or to indicate the unacceptability of carrying out the activity.

BRIEF DESCRIPTION OF THE DRAWINGS

The foregoing and other features of the various embodiments of the method and system described herein will become more apparent from the following detailed description and the accompanying drawings in which:

FIG. 11 is a chart showing a detailed example of a method of patient care governance as described herein, in particular a technique for assigning a numerical value or score to a patient's sleep, and also showing an unadjusted sleep threshold and an adjusted sleep threshold.

FIG. 13 is a chart showing example numerical values assigned to a menu of activities to signify the importance and sleep disruptive potential of the activities or of the consequences of the activities.

FIG. 17 is a chart similar to that of FIG. 11 but showing a method of patient care governance that depends on a quantified patient sleep history as a fraction of a maximum attainable sleep score.

DETAILED DESCRIPTION

Figure 1:
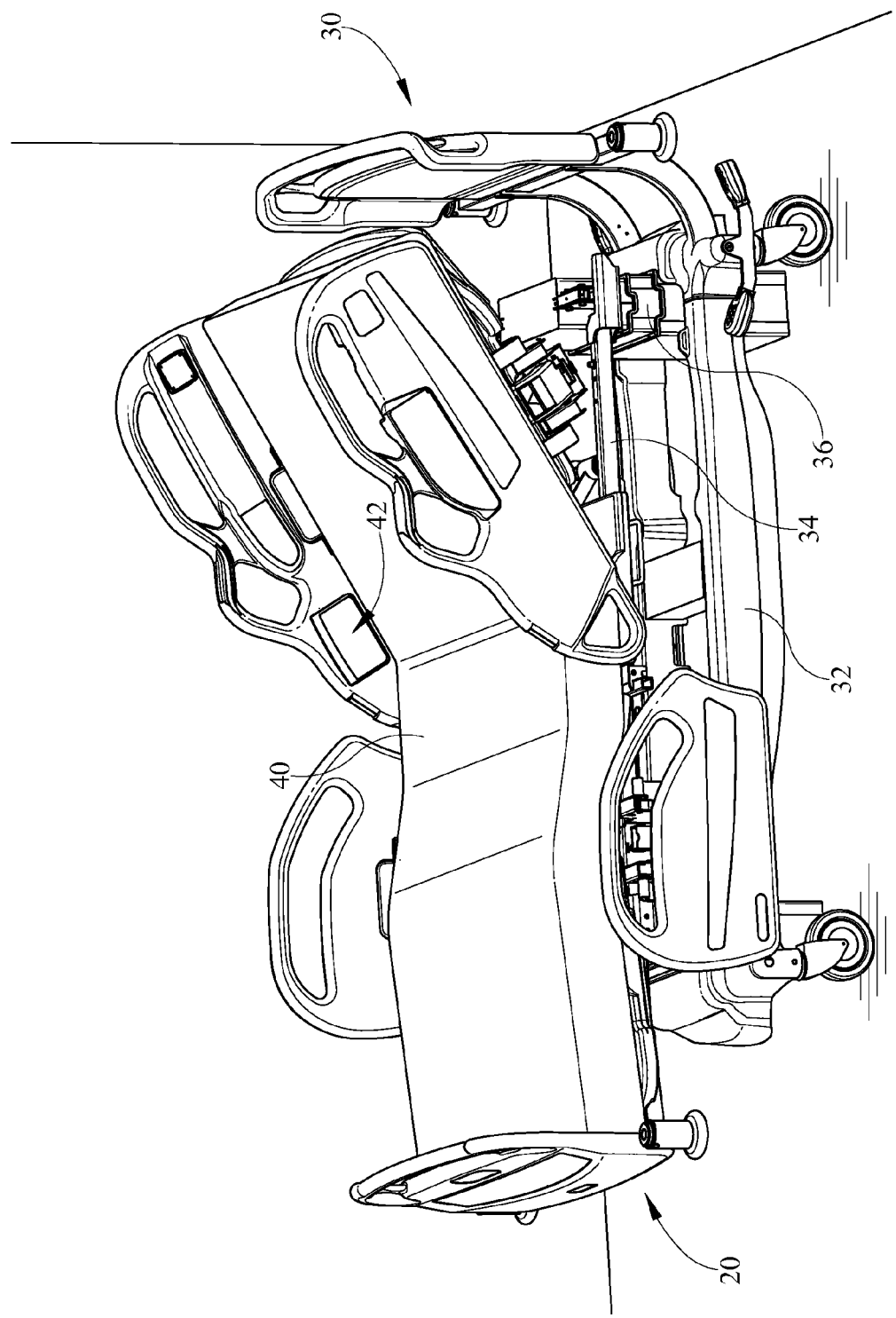
FIG. 1 is a perspective view of a hospital bed.
Figure 2:
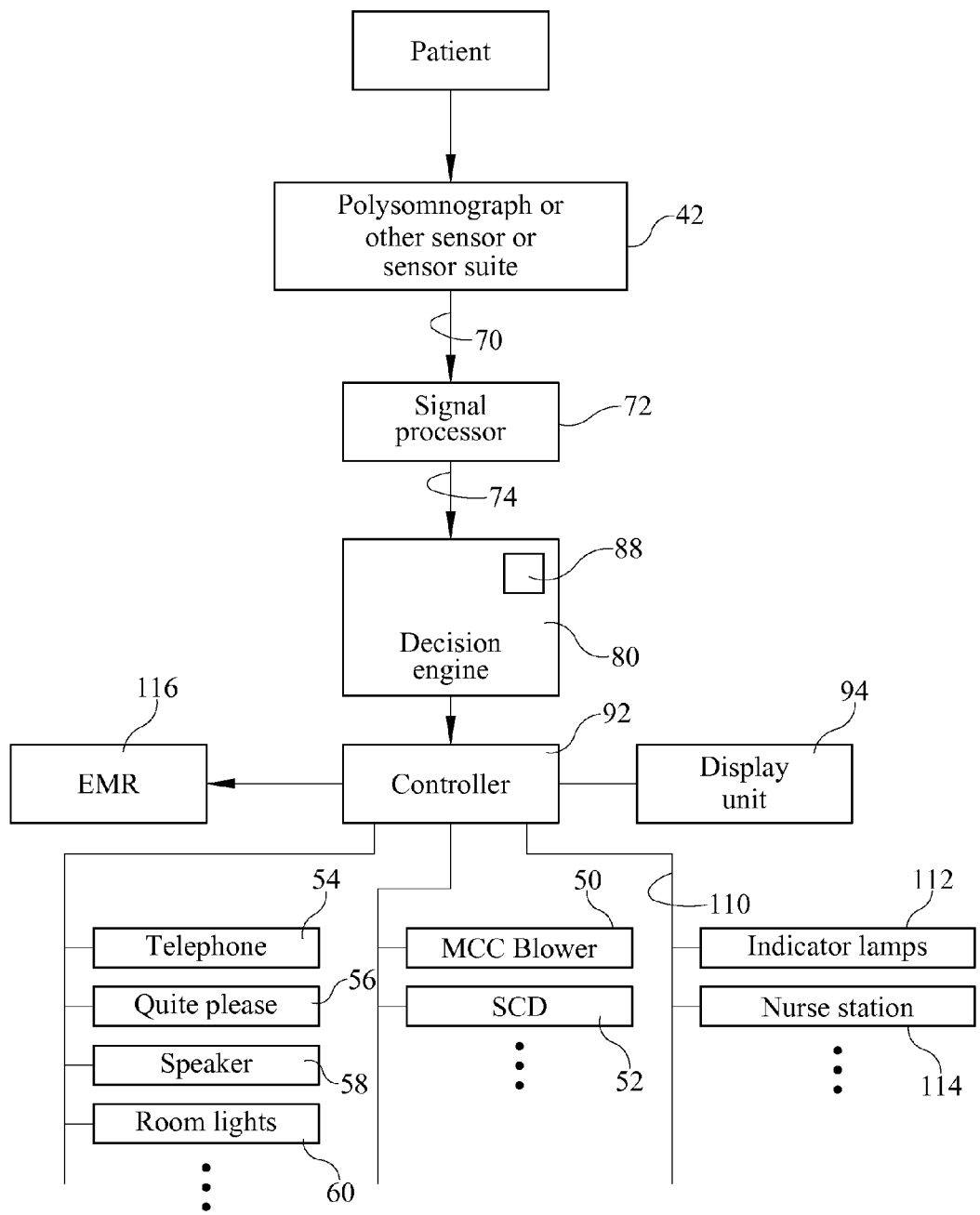
FIG. 2 is a diagram of a system for managing the sleep of a hospital patient with due consideration for the relative value of sleep and of the sleep disruptive potential and/or benefits of a candidate activity.

Referring to FIGS. 1-2, a hospital bed 30 comprises a base frame 32, an elevatable frame 34, and a lift system represented by head end and foot end canister lifts 36, only the head end one of which is visible, for raising and lowering the elevatable frame relative to the base frame. A mattress 40 rests on the elevatable frame. A polysomnograph 42 or other sensor or suite of sensors is provided to monitor the sleep related physiological parameters of a patient, not shown.

The bed, mattress or an item of auxiliary equipment may be able to provide certain therapies to the patient. In one example the mattress is a microclimate control (MCC) mattress that receives stream of air propelled by a blower 50 and guides the stream of air under the patient to keep the patient cool and dry. One mode of MCC operation is one that keeps the patient's skin temperature at or below 98 degrees F. but above 96 degrees F. Another mode of MCC operation is a mode that keeps the patient's skin temperature at or below 96 degrees F.

Another example is a Sequential Compression Device (SOD) 52 which is typically in the form of a sleeve that circumscribes the patient's lower leg. During use the sleeve is pressurized to help resist the formation of blood clots. The SCD is operable in a first, constant pressure mode in which the sleeve applies a constant pressure to the patient's leg. The SCD is also operable in a second, "high/fast" cyclic mode in which the sleeve pressure, and therefore the compression applied to the patient's leg, varies cyclically to a relatively high peak pressure at relatively high frequency. The SCD is also operable in a third, "low/slow" cyclic mode in which the sleeve pressure, and therefore the compression applied to the patient's leg, varies cyclically to a relatively low peak pressure at a relatively low frequency.

In another example the bed includes lateral rotation bladders that are inflatable and deflatable by a pneumatic system to gently turn the patient from side to side, a therapy known as continuous lateral rotation therapy (CLRT). The cycle parameters such as magnitude and frequency of the turn cycle and any pauses in the cycle are user adjustable and are under the command of a controller which allows a user to select the parameter values.

In another example the bed includes percussion bladders. The percussion bladders are supplied with pulses of pressurized air enabling them to apply vibrations to the patient at frequencies and amplitudes believed to be beneficial to a patient's lungs.

Each of the above activities are potentially therapeutic activities but also have the potential to interfere with the benefits of restorative sleep.

Other activities that are beneficial, but potentially disruptive of the patient's sleep include patient condition assessments such as assessing his level of pain and assessing the condition of his skin for the presence of incipient pressure ulcers or other abnormalities related to long-term bed occupancy, repositioning the patient, for example laterally turning the patient either-manually or semi-manually, and attending to or assisting with typical activities of daily living such as feeding, bathing and toilet visitation. Another beneficial activity is administering medications.

Other activities, such as facility maintenance work and housekeeping in the patient's room or in his care space within the room may not have any immediate, patient specific therapeutic or care management value, but are nevertheless necessary and have the potential to disrupt the patient's sleep.

Other activities do not necessarily have any intrinsic potential to disrupt the patient's sleep, but their consequences may have such potential. Examples include enabling or disabling a telephone 54 to accept incoming calls, illuminating or extinguishing a "Quiet Please" sign 56 outside the room, enabling or disabling speakers 58, and controlling room lights 60 or other ambient lights. These activities can typically be carried out with no disturbance to the patient's sleep. However the consequences of the activities (incoming phone calls, background noise, routine announcements over the speaker system, inappropriate light intensity) can be disruptive of Sleep.

Figure 3:
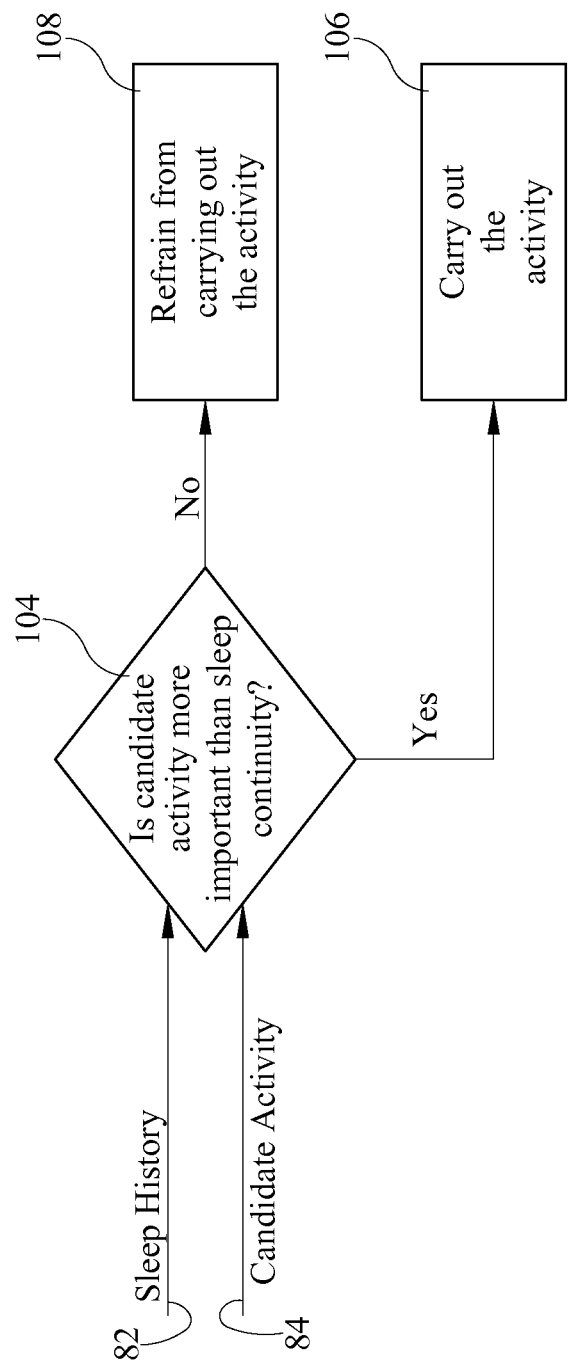
FIG. 3 is a block diagram showing an assessment of the benefit that a patient will realize from sleep relative to the benefit of a candidate activity and also showing the response to the assessment.

Readings 70 obtained by the polysomnograph are processed at signal processor 72 to extract the useful content of the readings. The processed signal 74 is provided to a decision engine 80. As seen at block 104 of the block diagram of FIG. 3, the decision engine employs the patient's sleep history 82 during the current sleep session to determine the importance of a candidate activity 84 relative to the importance of sleep continuity. Sleep history may include a record of sleep activity from the current sleep session preserved in a memory 88 or may be as simple as the patient's existing sleep state. If the candidate activity is more important than sleep continuity, the decision engine instructs a controller 92 to issue a command to carry out the activity or to indicate the acceptability of carrying out the activity (block 106). If the candidate activity is not more important than sleep continuity, the decision engine instructs the controller to refrain from carrying out the activity or to indicate the unacceptability or inadvisability of carrying out the activity (block 108).

As used herein, carrying out an activity includes initiating an activity not already underway, and continuing to carry out an already ongoing activity. Indicating the acceptability of carrying out the activity includes issuing a signal advising of the acceptability of the activity (e.g. illuminating a lamp 112 or sending a message 110 to a nurse station 114 or to an electronic medical record (EMR) 116, and enabling equipment features and/or functions related to carrying out the activity. Refraining from carrying out an activity includes declining to perform the activity, and immediate or delayed discontinuation of an activity already underway. Indicating the unacceptability of carrying out the activity includes issuing a signal advising of the unacceptability or inadvisability of the activity, and disabling equipment features and/or functions related to carrying out the activity.

Figure 4:
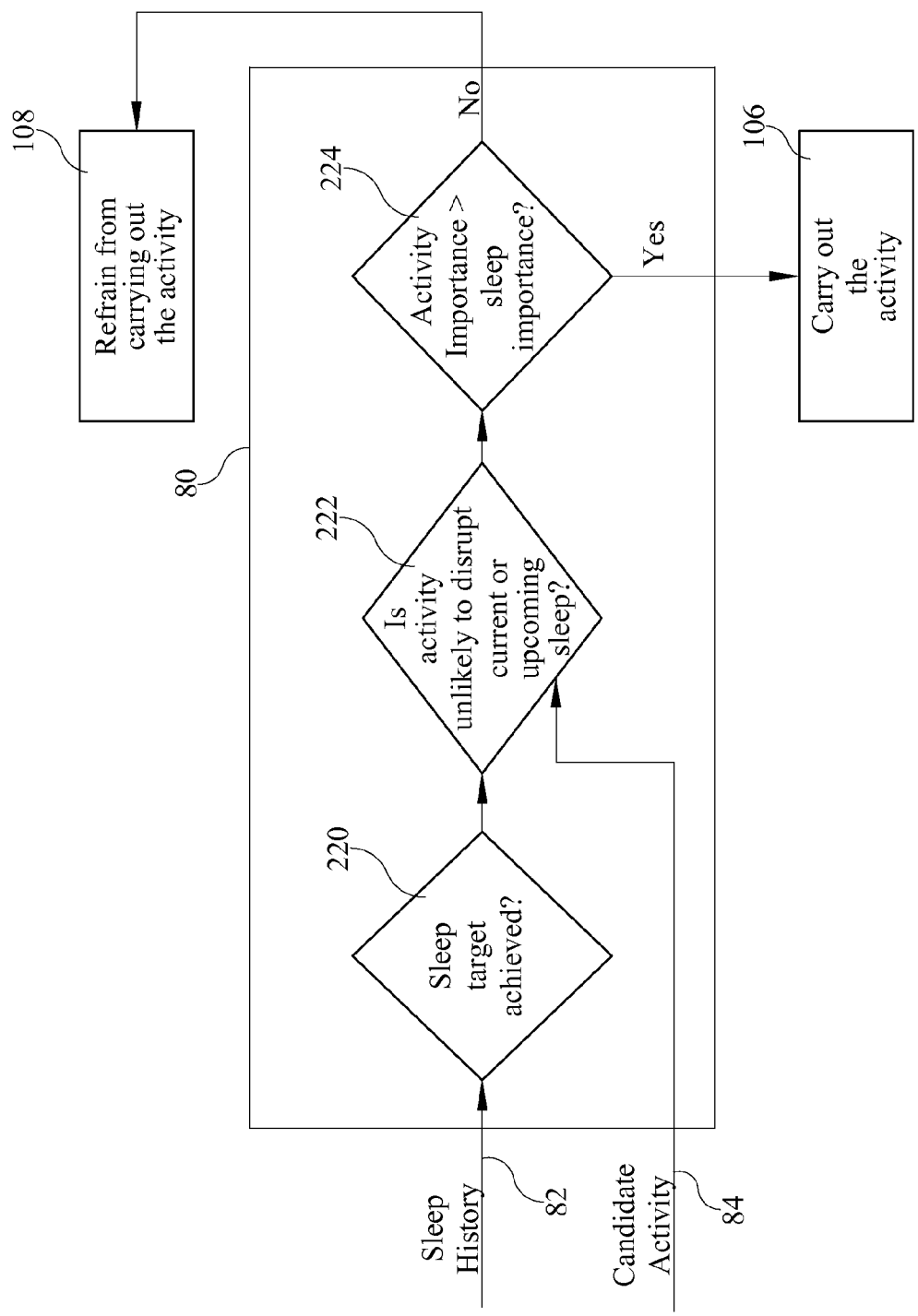
FIG. 4 is a block diagram showing an assessment of the patient's sleep history relative to a sleep threshold or target, an assessment of the sleep disruptive potential of a candidate activity, an assessment of the importance of the activity compared to the importance of sleep continuity, and the response to the assessments.

FIG. 4 shows a more detailed variant of the method in which the act of determining relative importance is a function of whether or not a sleep target or threshold has been achieved and the perceived likelihood that the candidate activity will disrupt the occupant's existing or upcoming sleep. Block 220 determines if the patient has achieved a sleep target or threshold. Block 222 then determines if candidate activity 84 is unlikely to disturb the patient's current or upcoming sleep. Block 224 assesses the importance of carrying out the candidate activity relative to the importance of continued sleep. If the importance of the activity exceeds that of continued sleep, the decision engine instructs controller 56 to issue a command to carry out the activity or to indicate the acceptability of carrying out the activity (block 106). If the candidate activity is no more important than sleep continuity, the decision engine instructs the controller to refrain from carrying out the activity or to indicate the unacceptability or inadvisability of carrying out the activity (block 108).

Figure 5:
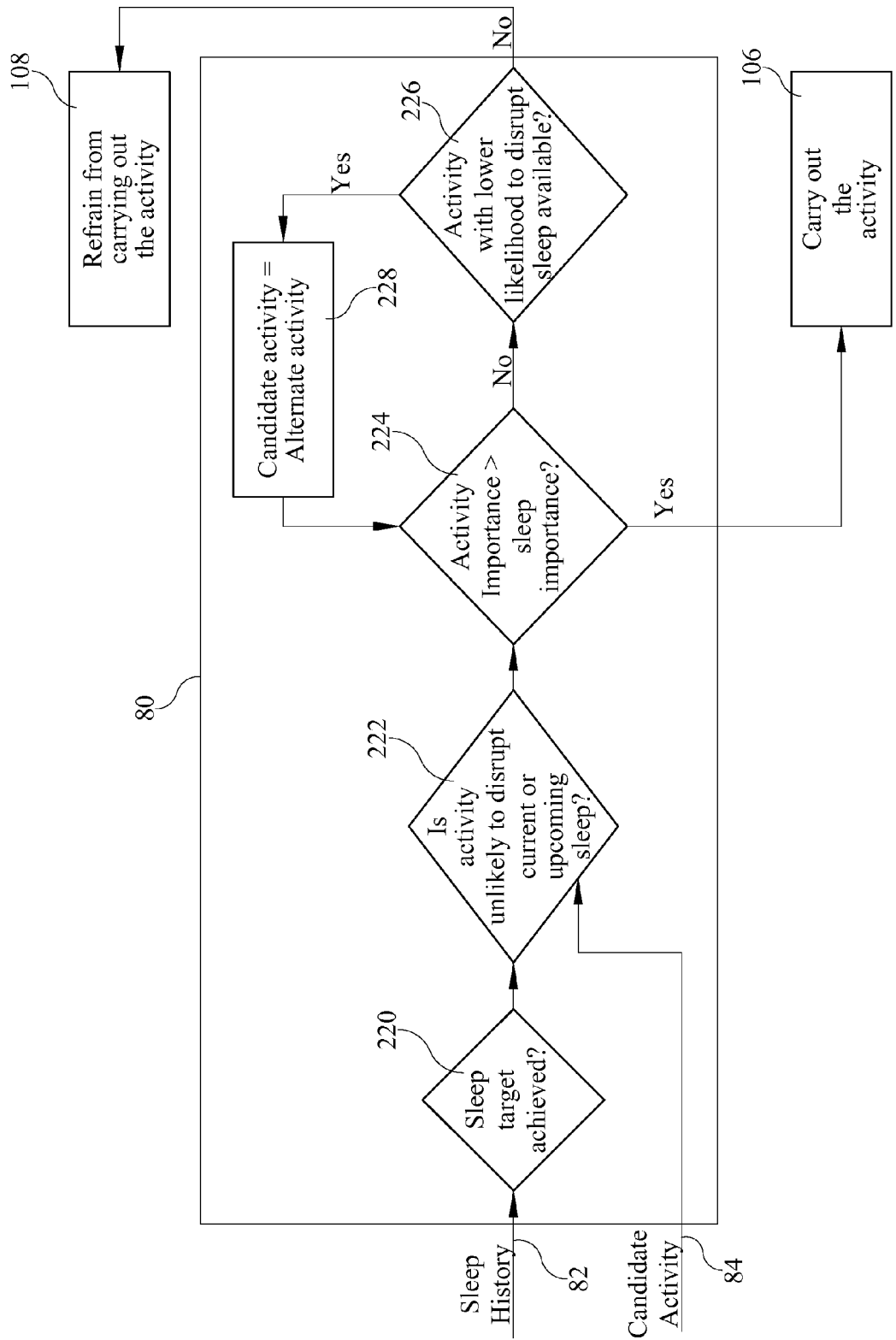
FIG. 5 is a block diagram similar to that of FIG. 4 in which the response depends on the possible availability of an alternate activity.

FIG. 5 shows a variant of the method of FIG. 4 in which the response to the determination of relative importance depends on the possible availability of an alternate activity. If block 224 determines that the importance of carrying out the candidate activity exceeds the importance of sleep, the decision engine instructs controller 56 to issue a command to carry out the activity or to indicate the acceptability of carrying out the activity (block 106). However if block 224 determines that the candidate activity is not more important than sleep continuity, the method proceeds to block 226 where it determines if an alternate activity with a lower likelihood of disturbing sleep is available. The alternate activity would ordinarily be a less disruptive variant of the previously evaluated candidate activity. If a less disruptive activity is available, the method proceeds to block 228 where it redesignates the candidate activity to be the alternate activity. The method then repeats the step at block 224 and, depending on the outcome, at block 226 until a satisfactory activity is identified or until all alternate candidate activities have been evaluated and found to be unsatisfactory. If a satisfactory activity is identified, the decision engine instructs controller 56 to issue a command to carry out the last evaluated activity or to indicate the acceptability of carrying out the last evaluated activity (block 106). If no satisfactory activity is identified the decision engine instructs the controller to refrain from carrying out the last evaluated activity or to indicate the unacceptability or inadvisability of carrying out the last evaluated activity (block 108).

Figure 6:
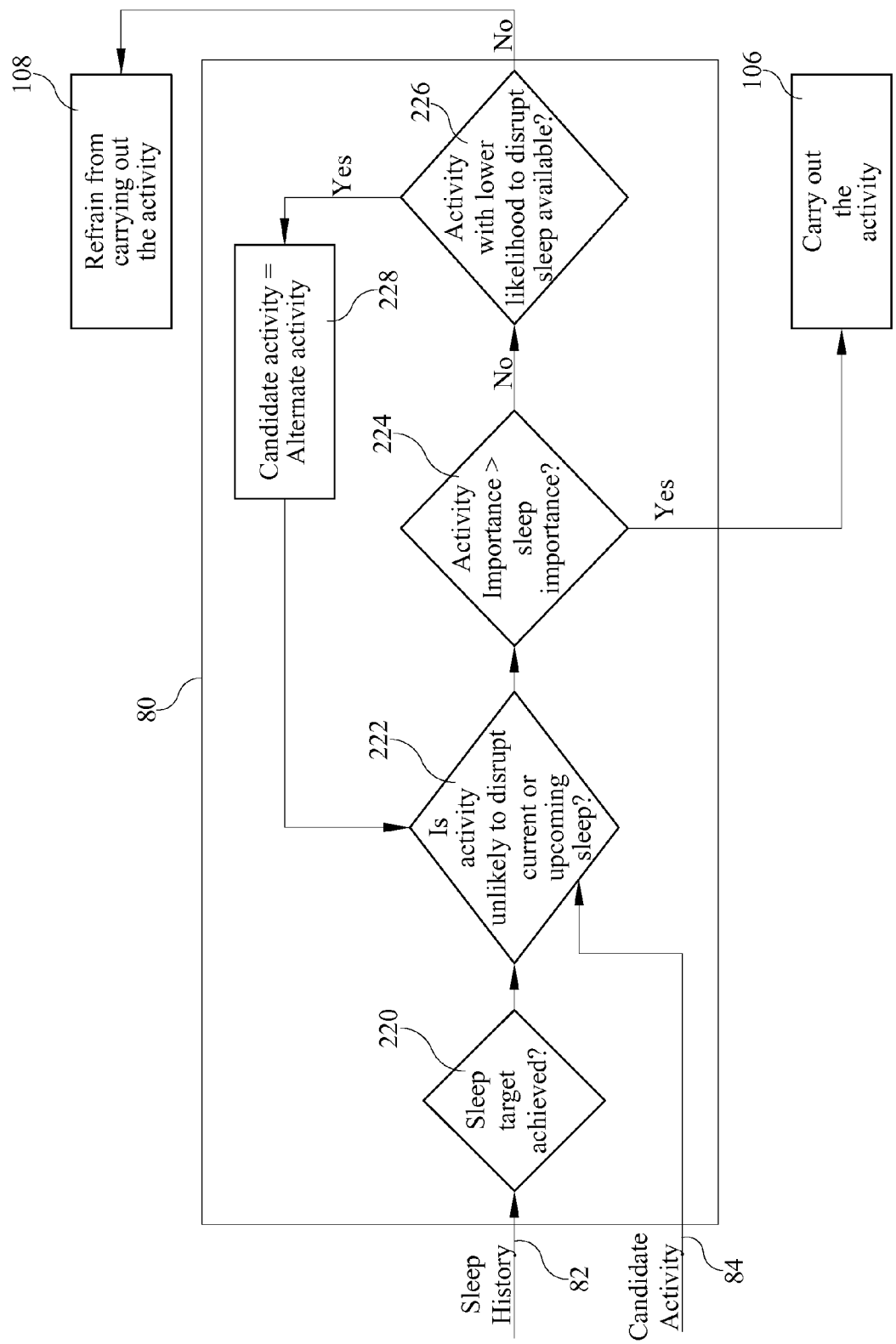
FIG. 6 is a block diagram similar to that of FIG. 5 showing a different response to the possible availability of an alternate activity.

FIG. 6 is a block diagram similar to that of FIG. 5 showing a different response to the possible availability of an alternate activity. In FIG. 6, the output of block 228 proceeds to block 222 rather than to block 224. The method then repeats the steps at blocks 222 and 224 and, depending on the outcome, at block 226 until a satisfactory activity is identified or until all alternate candidate activities have been evaluated and found to be unsatisfactory.

Figure 7:
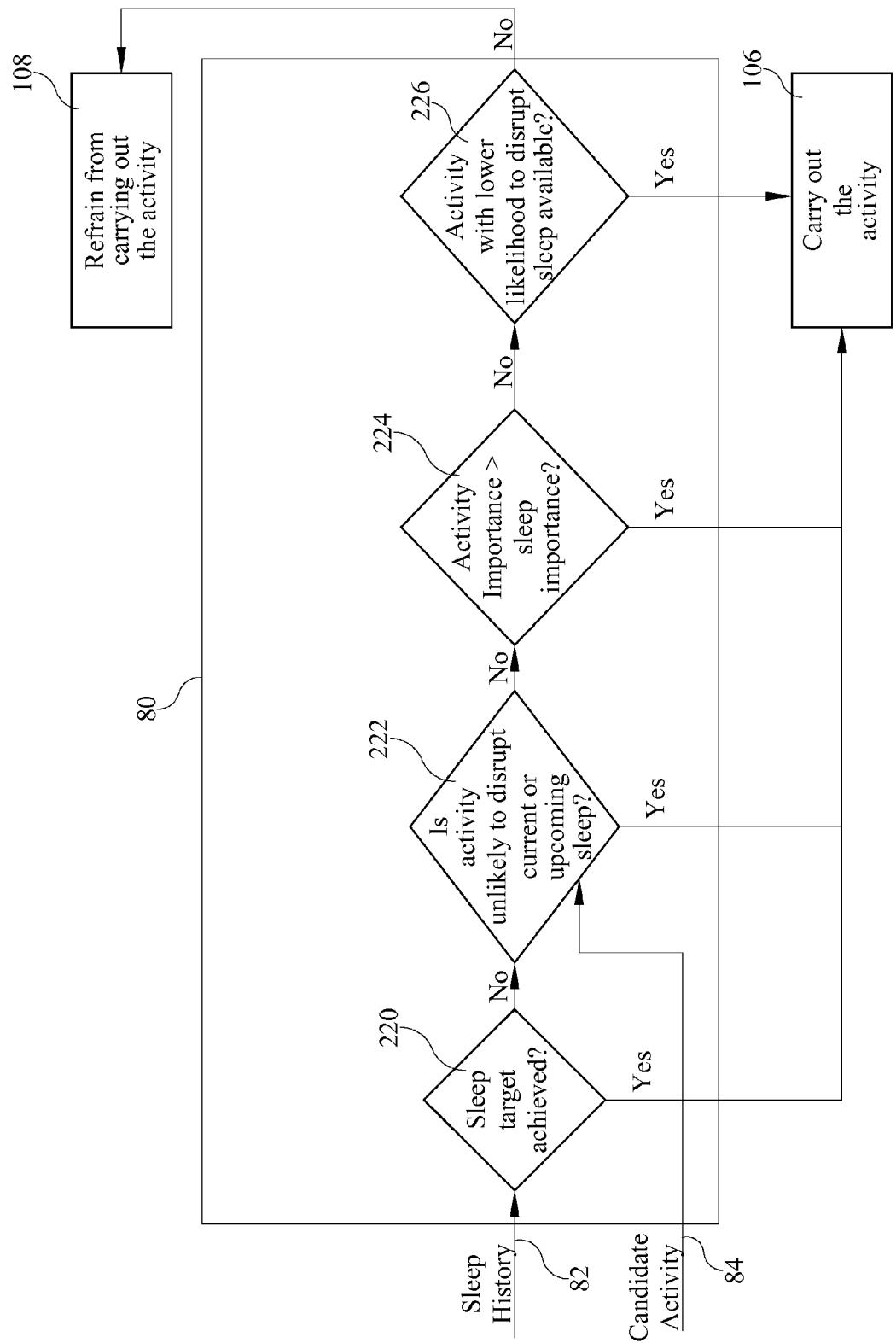
FIG. 7 is a block diagram similar to that of FIG. 5 showing additional pathways available as a result of the assessments and also showing an available alternate activity being carried out unconditionally.

FIG. 7 is a block diagram similar to that of FIG. 6 showing additional pathways available as a result of the assessments. Block 220 determines if the patient has achieved a sleep target or threshold. If so, the method proceeds to block 106 where the decision engine instructs controller 56 to issue a command to carry out the activity or to indicate the acceptability of carrying out the activity. If not, the method proceeds to block 222 which determines if the candidate activity is unlikely to disturb the patient's current or upcoming sleep. If so, the method proceeds to block 106. If not the method proceeds to block 224 which assesses the importance of carrying out the candidate activity relative to the importance of continued sleep. If the importance of the activity exceeds that of continued sleep the decision engine instructs controller 56 to issue a command to carry out the activity or to indicate the acceptability of carrying out the method. Otherwise the method proceeds to block 226 where it determines if an alternate activity with a lower likelihood of disturbing sleep is available. The alternate activity would ordinarily be a less disruptive variant of the previously evaluated candidate activity. If so, the method unconditionally proceeds to block 106.

Figure 8:
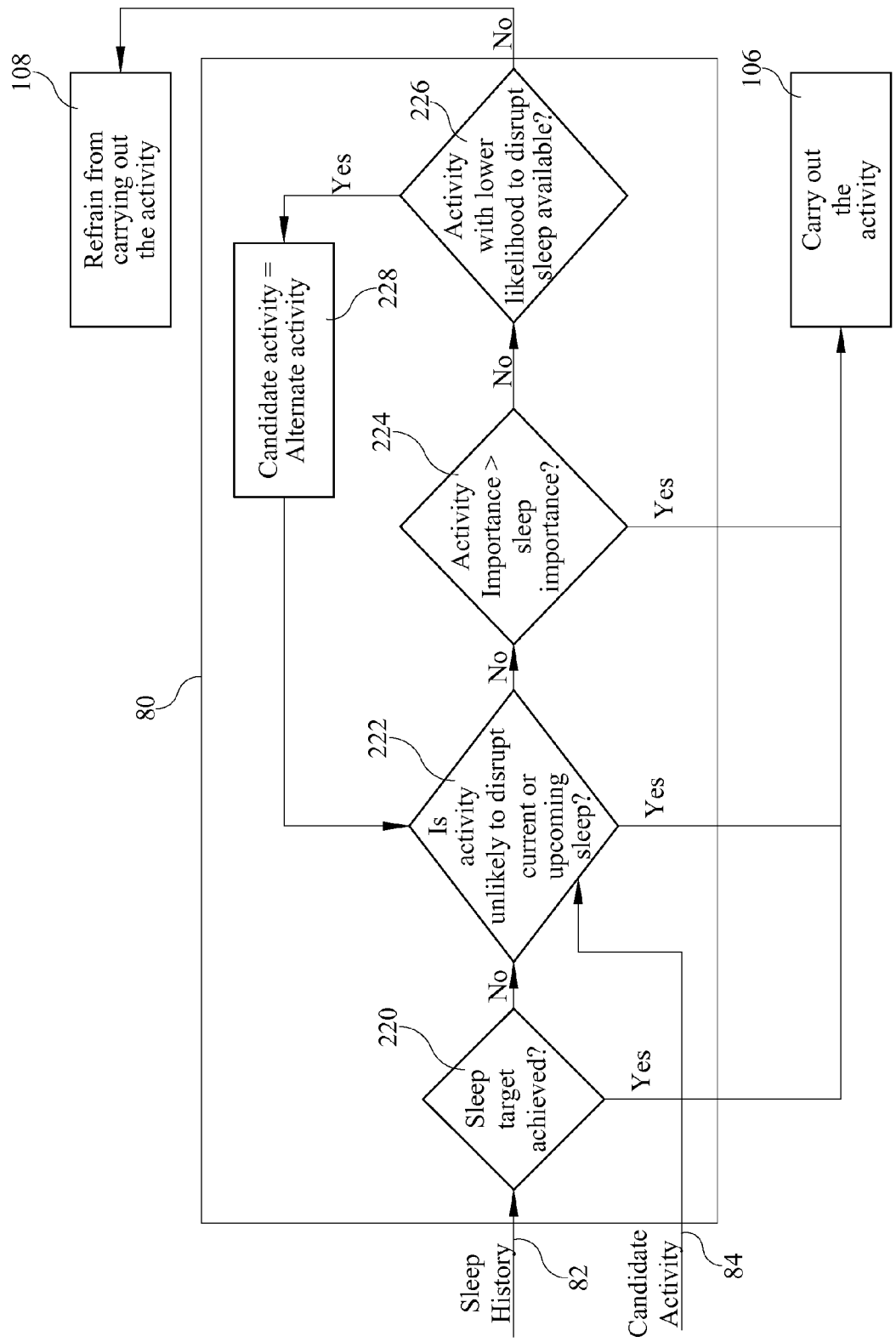
FIG. 8 is a block diagram similar to that of FIG. 7 showing one option for evaluating a possible alternate activity.

FIG. 8 is a block diagram similar to that of FIG. 7 showing one option for evaluating a possible alternate activity. Block 220 determines if the patient has achieved a sleep target or threshold. If so, the method proceeds to block 106 where the decision engine instructs controller 56 to issue a command to carry out the activity or to indicate the acceptability of carrying out the activity. If not, the method proceeds to block 222 which determines if the candidate activity is unlikely to disturb the patient's current or upcoming sleep. If so, the method proceeds to block 106. If not the method proceeds to block 224 which assesses the importance of carrying out the candidate activity relative to the importance of continued sleep. If the importance of the activity exceeds that of continued sleep the method proceeds to block 106. Otherwise the method proceeds to block 226 where it determines if an alternate activity with a lower likelihood of disturbing sleep is available. The alternate activity would ordinarily be a less disruptive variant of the previously evaluated candidate activity. If a less disturbing activity is available, the method proceeds to block 228 which redesignates the candidate activity to be the alternate activity. The method then repeats the steps at blocks 222 and/or 224 and, depending on the outcome, at block 226 until a satisfactory activity is identified or until all alternate candidate activities have been evaluated and found to be unsatisfactory.

Figure 9:
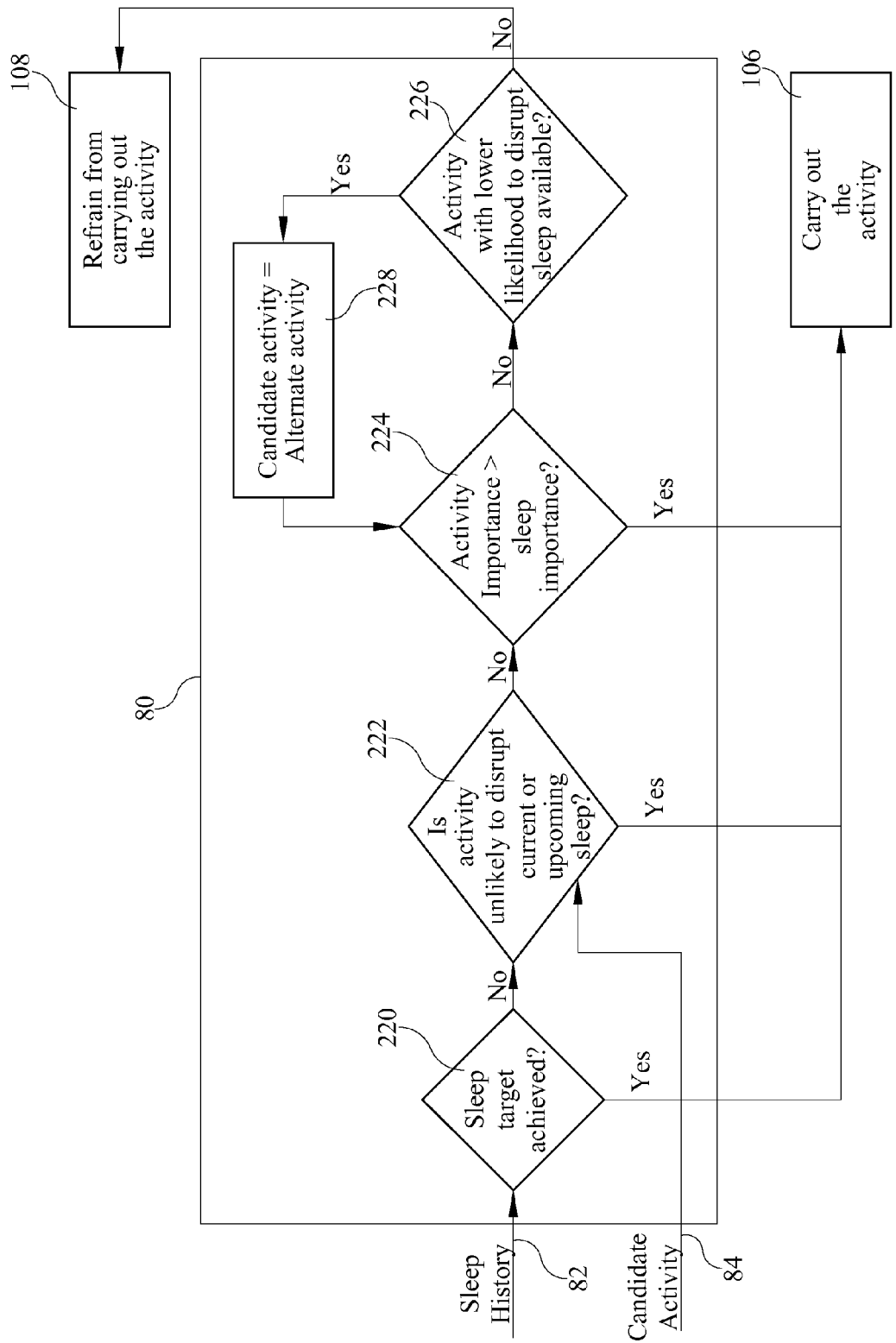
FIG. 9 is a block diagram similar to that of FIG. 8 showing another option for evaluating a possible alternate activity.

FIG. 9 is a block diagram similar to that of FIG. 8 showing another option for evaluating a possible alternate activity. The method is the same as the method of FIG. 8 except that after redesignation step 228 the method proceeds to block 224 rather than to block 222. The method repeats the determining step at block 224 and, depending on the outcome, step 226 until a satisfactory activity is identified or until all alternate candidate activities have been evaluated and found to be unsatisfactory.

Figure 10:
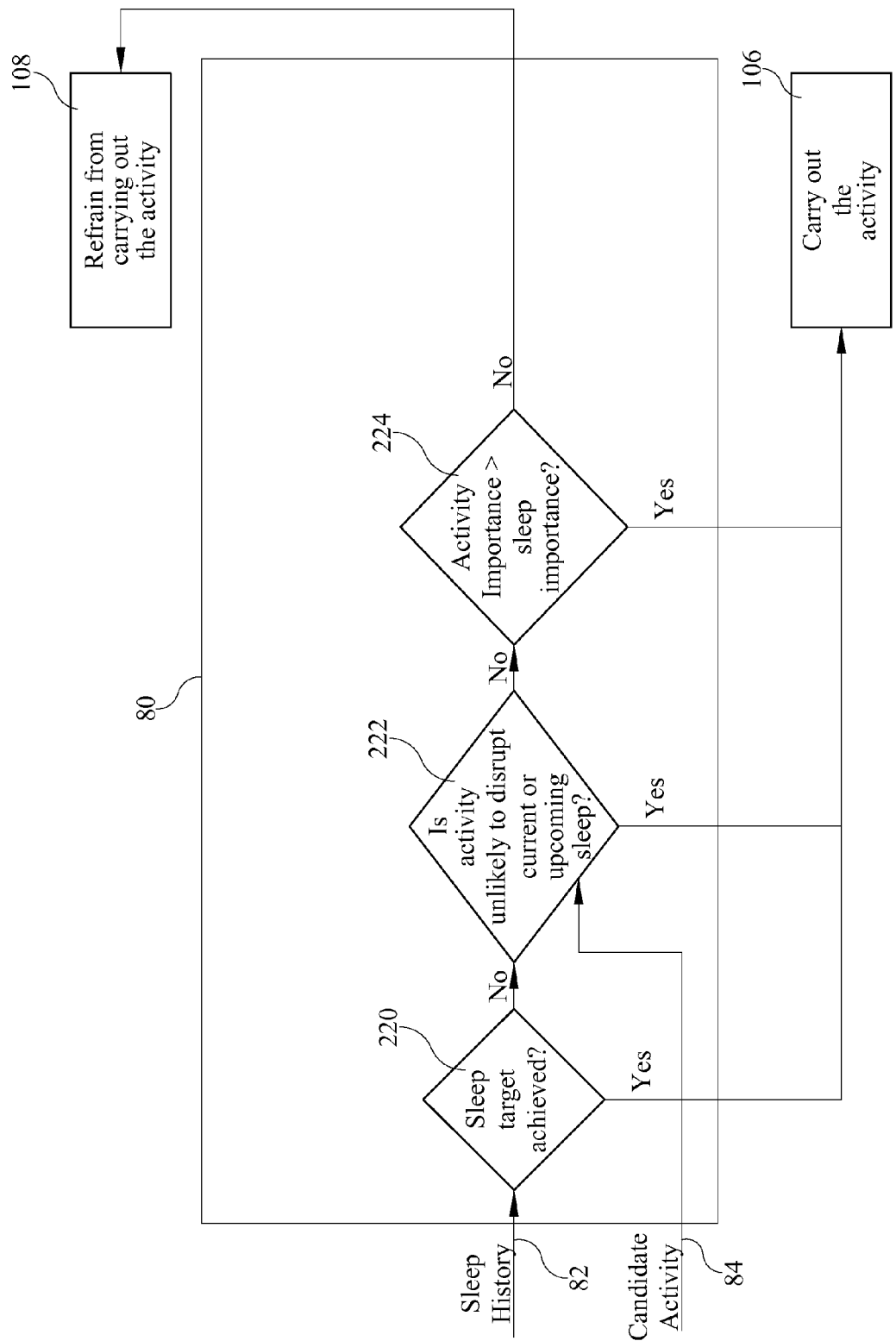
FIG. 10 is a block diagram similar to those of FIGS. 7-9 but which does not account for the possible availability of an alternate activity.

FIG. 10 is a block diagram similar to that of FIGS. 7-9 in which block 226 is absent and a "NO" outcome at block 224 causes the method to proceed to block 108.

Figure 12:
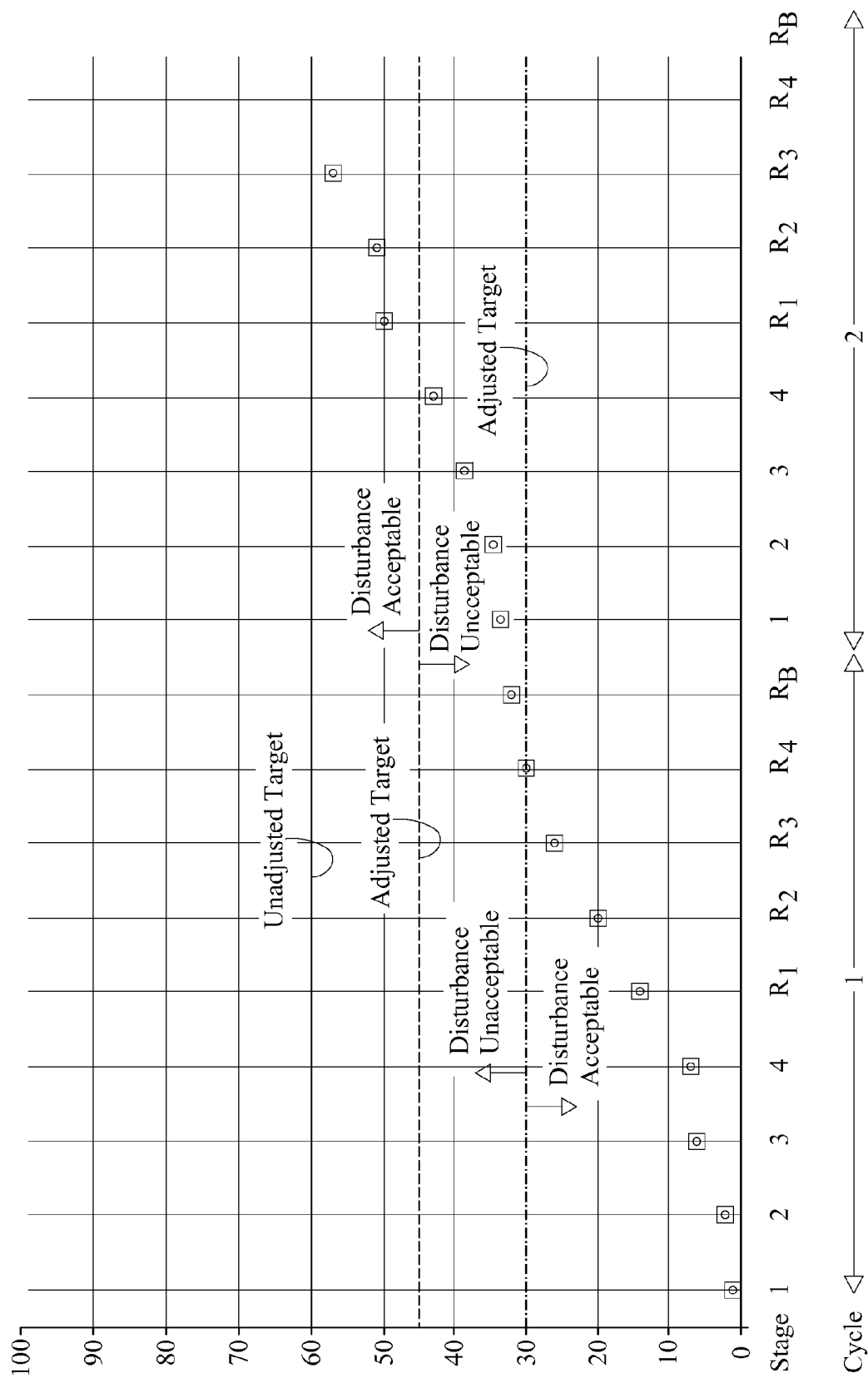
FIG. 12 is a graph showing, as a function of sleep stage, the patient's sleep history, the unadjusted threshold of FIG. 11, the adjusted threshold of FIG. 11 interpreted as a "disturb after" threshold (dashed line), and a second adjusted threshold interpreted as a "disturb before" threshold (dash-dot line).

FIGS. 11 and 12 show a detailed example of the method of patient care governance. Referring first to FIG. 11 a sleep session is divided into cycle numbers (column 1) and sleep stages within each cycle (col. 2). The REM stage is divided into REM subdivisions or substages denoted as REM1, REM2 and so forth. Column 3 shows a duration dependent numerical value assigned to each sleep stage on a scale of zero to five depending on the perceived restorative value of achieving a minimum duration of sleep in each sleep stage. Column 4 shows a duration independent numerical value assigned to each sleep stage with some stages being weighted more heavily than others. Column 5 shows the duration, in minutes, that it is desired for the patient to experience the indicated sleep stage during a sleep session. In the example, stages 1 and 2 are perceived to have no appreciable restorative value and therefore do not have any desired duration. Stage 3 has a desired duration of 25 minutes and a duration dependent value of 3. Stage 4 has a desired duration of 10 minutes and a duration dependent value of 4. The first seven minute segment of REM (REM substage REM1) has a duration dependent value of 5. The next 12 minutes of REM (REM2) have a duration dependent value of 4. The next 20 minutes of REM (REM3) have a duration dependent value of 3. The next 25 minutes of REM (REM4) have a duration dependent value of 2. The balance of time spent in REM sleep, if any, has a duration dependent value of 1.

Column 6 of FIG. 11 and the data symbols on the graph of FIG. 12 (which are from column 9 of FIG. 11) show the patient's sleep history during the current sleep session. In particular column 6 shows whether or not the patient achieved the minimum desired duration of sleep (the sleep target) of each sleep stage. The "Not Applicable" (N/A) entries for stages 1 and 2 reflect the zero value assigned to stage 1 and 2 sleep. The "Yes" entries for stage 3 and for REM substages REM1, REM2, REM3 and REM4 reflect that the patient experienced at least the desired 25 minutes of stage 3 sleep and at least the desired 7, 12, 20 and 25 minutes of sleep in substages REM1, REM2, REM3 and REM4. The "Yes" entry corresponding to "Balance of REM" reflects that the patient spent some additional time in the REM stage before transitioning to cycle 2. The "No" entry for stage 4 reveals that the example patient did not complete 10 minutes of stage 4 sleep. Similar interpretations apply to the entries for the various sleep stages of cycle 2. The absence of entries after REM3 of cycle 2 indicate that those sleep stages have not been completed in the current sleep session, i.e. the patient has not yet completed the required 25 minutes of sleep in the REM4 substage.

Columns 7 and 8 are duration dependent and duration independent scores credited to the patient. Each duration dependent score is either the numerical equivalent of the duration dependent sleep value of column 3 or is zero for stages having no value (stages 1 and 2) and for stages in which the patient did not receive the duration of sleep specified in column 5 (stage 4 of cycle 1). The duration independent score is a credit for having passed through the stage irrespective of the amount of time spent in that stage. The duration independent score equals the stage specific, duration independent sleep stage value of column 4 and therefore reflects differences in weighting (i.e.) value among the stages.

Column 9 is a cumulative score, i.e. the sum of the duration dependent and duration independent scores for the indicated stage and all previous stages. The cumulative score is the score represented by the data symbols on the graph of FIG. 12.

Columns 10-11 show the development of a sleep threshold or target for a candidate activity. Column 10 shows a baseline or unadjusted sleep threshold having a magnitude of 60 (solid line of FIG. 12). The unadjusted threshold is adjusted up or down by a scale factor (described below) depending on the importance of a candidate activity and the sleep disruptive potential of that activity in order to obtain an actual or adjusted threshold (column 11). The chart shows an adjusted threshold of 45; the graph of FIG. 12 shows two adjusted thresholds, one having a value of 45, the other a value of 30.

Figure 14:
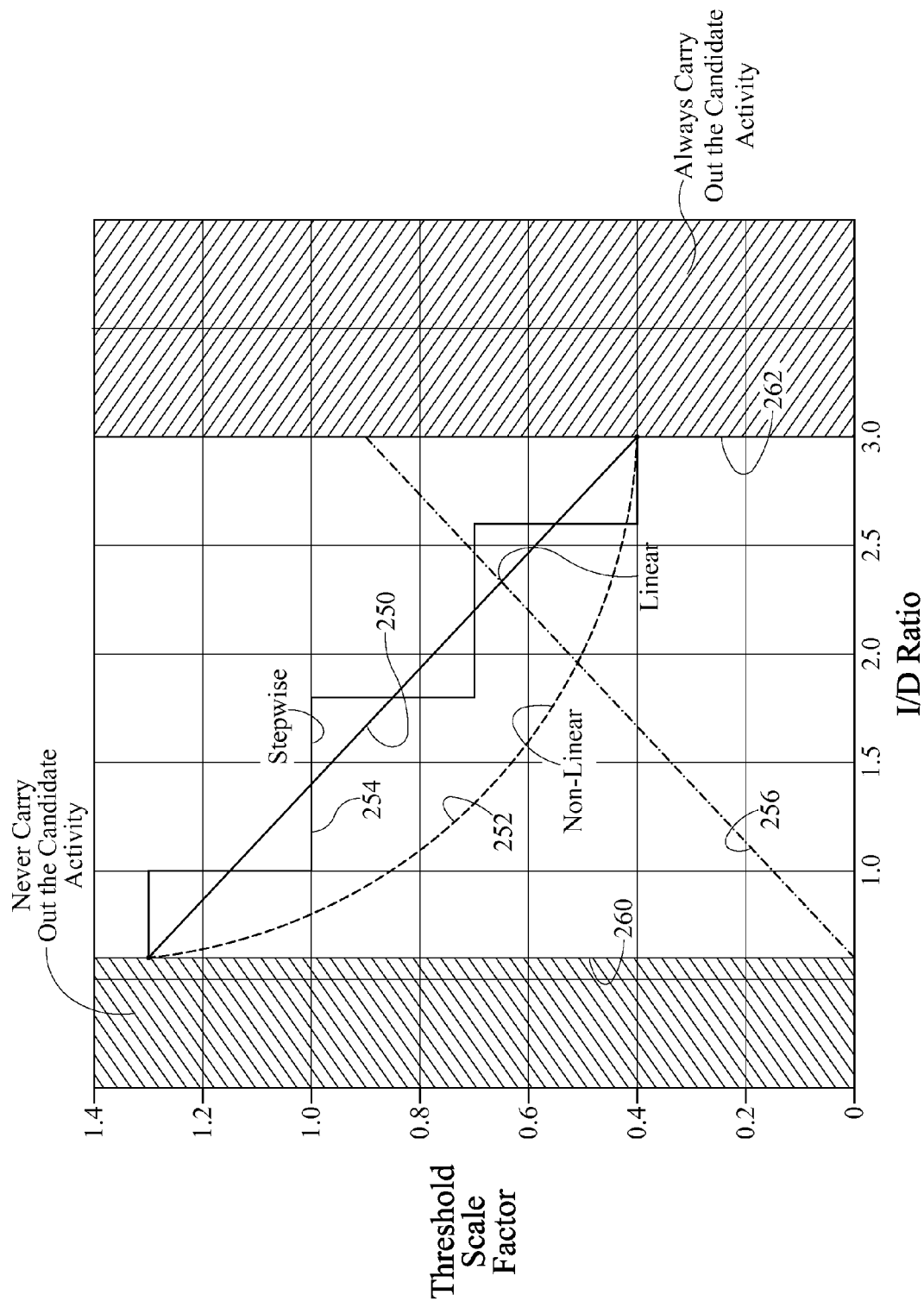
FIG. 14 is a graph illustrating examples of scale factors to be applied to an unadjusted sleep threshold to determine an adjusted sleep threshold reflecting the importance and sleep disruptive potential of the activity or of the consequences of the activity.

FIGS. 13-14 show one way of determining the scale factor to be applied to the unadjusted threshold as a function of the perceived importance and perceived sleep disruptive potential of several activities. Referring to FIG. 13, column A lists a nonexhaustive menu of candidate activities. Each activity is assigned an importance (column B) on a scale of zero to five with zero signifying no importance and five signifying highest importance. Each activity is also assigned a numerical value to indicate its sleep disruptive potential on a scale of zero to three where zero signifies no disruptive potential and three signifies highest disruptive potential (column C). As discussed previously the disruptive potential of certain activities is not intrinsic to the activity but instead is associated with the consequences of having conducted the activity (e.g. enabling a phone to receive incoming calls). Column D is the ratio of importance of the candidate activity to sleep disruptive potential of the candidate activity, I/D. FIG. 14 is a graph showing an example scale factor as a linear function 250 of I/D ratio. Other relationships such as nonlinear 252 or stepwise 254 may also be used. An activity judged to have no sleep disruptive potential (e.g. operating an SCD device in a constant pressure mode) is assigned an I/D ratio greater than the highest calculated I/D ratio. Activities having an I/D ratio less than a lower limit 260 or greater than an upper limit 262 can be designated as activities that should never be carried out or that should always be carried as indicated by the crosshatched regions of FIG. 14. The activity of assisting a patient with a toilet visit has been intentionally assigned an unrealistically low sleep disruptive potential in order to force its I/D ratio to always fall into the rightmost crosshatched region of FIG. 14.

For a given activity the I/D ratio is used to determine the scale factor. The unadjusted sleep threshold (FIG. 11, col. 10 and FIG. 12 solid line) is then multiplied by the scale factor to obtain the adjusted threshold (FIG. 11, col. 11 and FIG. 12 dashed line). In the example of FIG. 12 a scale factor of 0.75, corresponding to an I/D ratio of approximately 2.0 (using the linear relationship 250) was applied to the baseline threshold value of 60 to obtain an adjusted or actual threshold value of 45. An activity that corresponds to this threshold is operating a microclimate control (MCC) system in a mode intended to maintain patient skin temperature at or below 96 degrees F. (FIG. 13)

The importance of the candidate activity relative to the importance of uninterrupted sleep is determined by comparing the patient's sleep score to the adjusted threshold. If the candidate activity is more important than sleep continuity, the activity is carried out or the acceptability of carrying out the activity is indicated. If the candidate activity is no more important than sleep continuity, the system or caregiver refrains from carrying out the activity or an indication is made that carrying out the activity is unacceptable or inadvisable.

According to one possible protocol it is considered inadvisable to disturb a bed patient to carry out an activity until after the patient's sleep score is at least as high as the threshold. This can be referred to as a "disturb after" protocol because of the perceived inadvisability of disturbing the patient to carry out the activity until after his sleep score has attained the threshold value. For example, referring to FIG. 12, in which the activity corresponding to the adjusted threshold (dashed line) is operating the MCC system in the "96 degree mode", the activity would not be carried unless and until the patient had entered the first REM substage of the second cycle. A higher I/D activity could be conducted sooner because its scale factor is lower (FIG. 13). Conversely a lower I/D activity would be delayed or deferred due to its higher scale factor.

An alternative protocol is one in which it is considered acceptable to disturb a bed patient to carry out an activity at any time before he has achieved a sleep score of at least as much as the threshold. This can be referred to as a "disturb before" protocol because of the perceived acceptability of disturbing the patient before his sleep score has attained the threshold value. The "disturb before" threshold may be the same as the above described "disturb after" threshold, or may be different but would likely not be higher than the "disturb after" threshold, FIG. 14 shows a linear scale factor 256 as a function of I/D ratio (dash-dot line) that, when applied to the baseline threshold, establishes a "disturb before" threshold. Once again using the unadjusted threshold of 60, and considering an activity whose I/D ratio is 2.0, the adjusted threshold is 30 (the unadjusted threshold (60) multiplied by a scale factor of 0.5 (from FIG. 14 at I/D=2.0)). As seen in FIG. 12 where the threshold is a dash-dot line, it would be considered acceptable to carry out the candidate activity at least up to REM3 and possibly up to REM4 of the first cycle, but not after REM4. A higher I/D ratio activity corresponds to a higher scale factor thereby elevating the "disturb before" threshold so that the higher I/D activity is acceptable later in the sleep session than is the first considered activity. Conversely a lower I/D ratio activity corresponds to a lower scale factor thereby lowering the "disturb before" threshold so that the lower I/D activity is acceptable only for a shorter portion of the sleep session than is the first considered activity.

Figure 15:
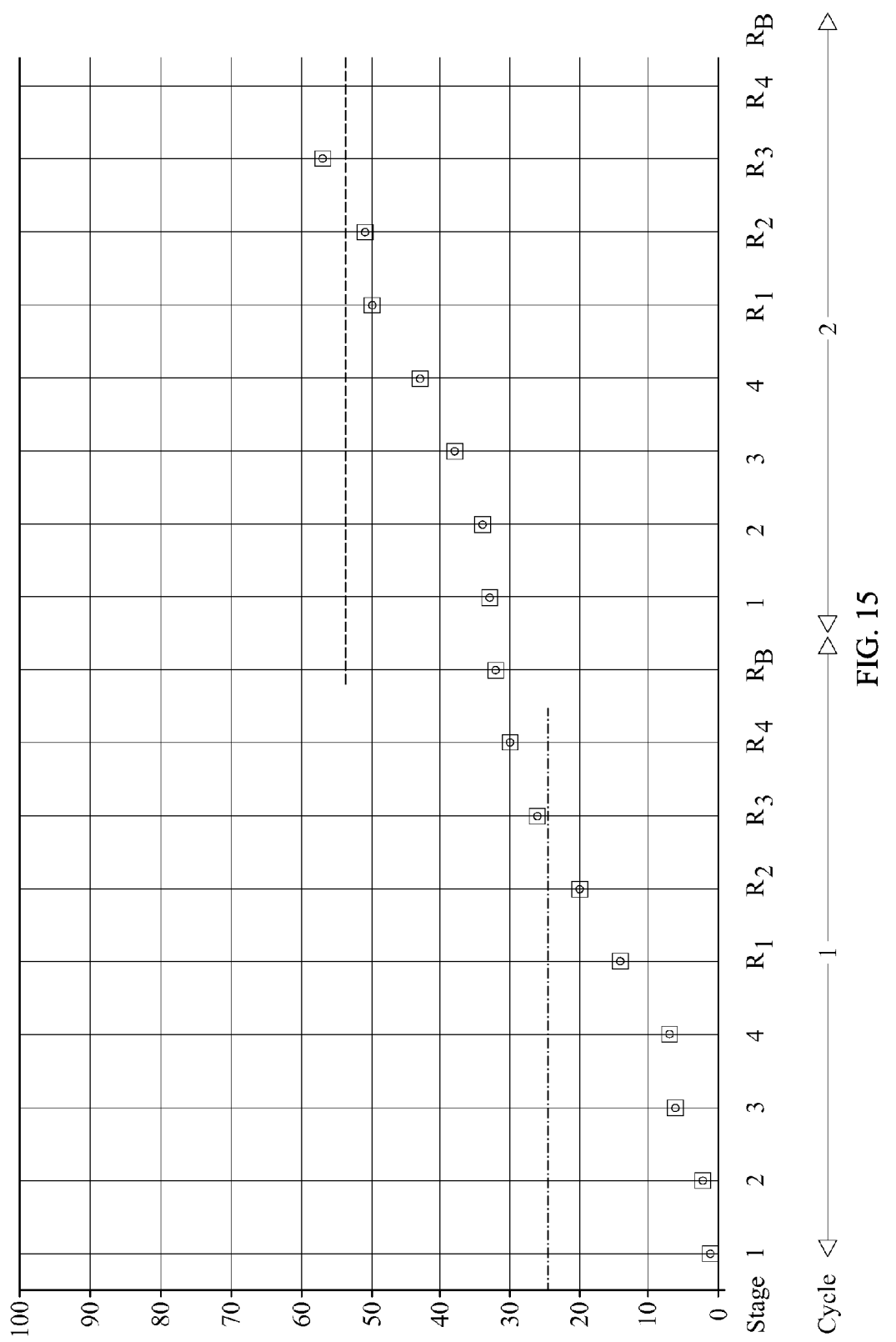
FIG. 15 is a graph similar to that of FIG. 12 showing combined use of a "disturb after" threshold and a "disturb before" threshold.

FIG. 15 shows another protocol using both a "disturb" before and a "disturb after" threshold. In the illustrated example a "disturb before" threshold of 24 is in effect through REM4 of cycle 1. Afterwards a "disturb after" threshold of 53 is invoked. These thresholds correspond to an unadjusted threshold of 60, and an activity having an I/D ratio of about 1.7 (e.g. administering medication "A") which corresponds to a "disturb before" scale factor of about 0.4 and a "disturb after" scale factor of about 0.88 based on the linear relationship of FIG. 13. As seen in FIG. 14 it is considered acceptable to disturb the patient up to and including REM2 of cycle 1 to administer medication "A". Afterwards it is considered unacceptable or inadvisable to disturb the patient to administer medication "A" until after REM2 of cycle 2. If desired multiple "disturb before" and "disturb after" thresholds could be used during a single sleep session.

Figure 16:
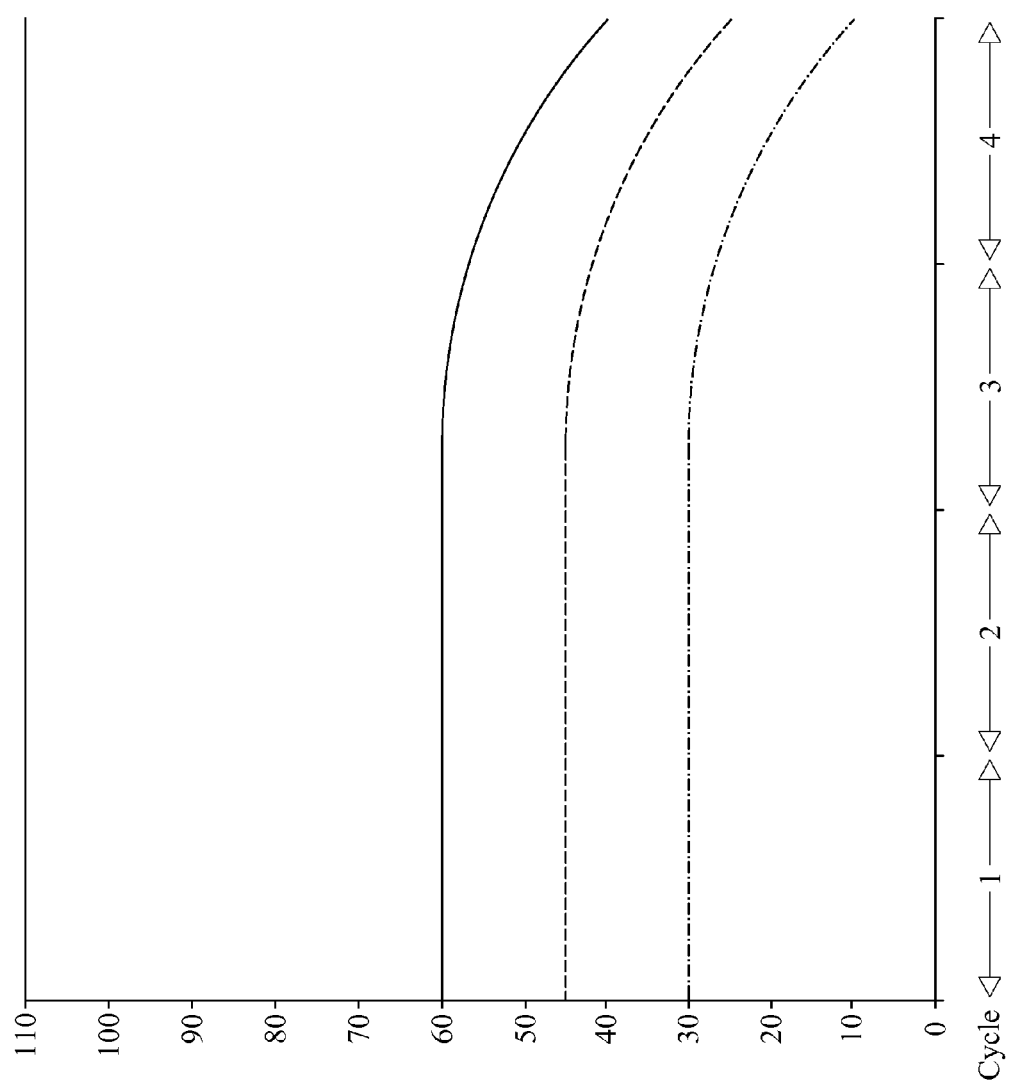
FIG. 16 is a graph similar to that of FIG. 12 showing non-constant thresholds.

In each of the above described protocols, each unadjusted threshold was a constant. By contrast FIG. 16 shows a nonconstant unadjusted threshold (solid line) and corresponding adjusted thresholds based on a "disturb after" scale factor of 0.75 (dashed line) and a "disturb before" scale factor of 0.50 (dash-dot line).

Figure 18:
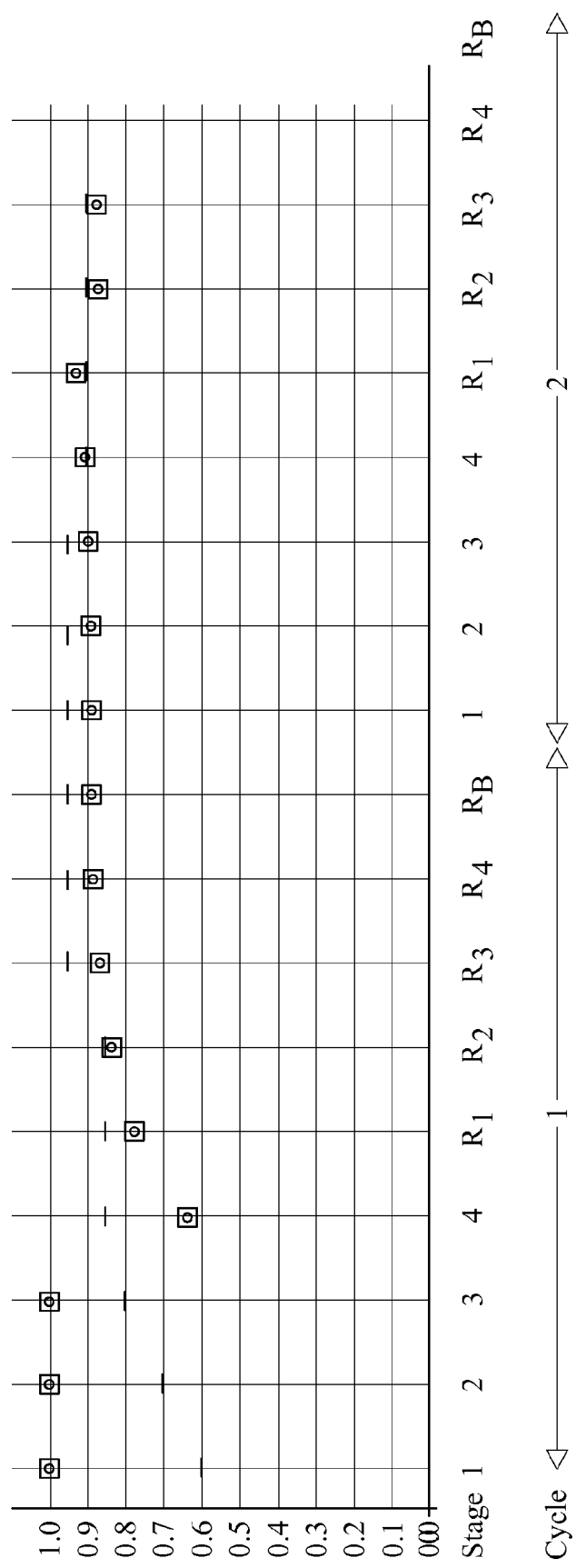
FIG. 18 is a graph showing, as a function of sleep stage, the patient's sleep history and the sleep threshold of FIG. 17.

FIGS. 17-18 show an example in which patient care governance depends on a quantified patient sleep history as a fraction of a maximum attainable sleep score. Only the first two cycles of the sleep session are illustrated. The example is the same as that of FIG. 11 except that column 6 (of FIG. 11), which indicates whether or not the patient has achieved the prescribed number of minutes of a given sleep stage, has been replaced by new columns 10-13. Column 10 is the maximum attainable sleep score, i.e. the cumulative sum of the duration dependent sleep value (column 3) and the duration independent sleep value (column 4). Column 11 and the data symbols of FIG. 18 show the sleep score that the patient has attained expressed as a fraction of the maximum attainable score. Column 12 and the short horizontal bars of FIG. 18 show a sample "disturb after" sleep target or threshold. For example in cycle 1 stage 1 it would be acceptable to disturb the patient to carry out a candidate activity only if he had achieved 60% of the maximum cumulative sleep score. If the patient were in cycle 1 stage 2 sleep it would be acceptable to disturb the patient to carry out the candidate activity only if he had achieved 70% of the maximum cumulative sleep score. Column 13 shows that it is justifiable to disturb the patient to carry out the candidate activity through stage 3 of cycle 1 and in stage 4 and REM1 of cycle 2 because he has achieved the required fraction of sleep. From stage 4 of cycle 1 through stage 2 of cycle 2 and during REM2 and REM3 of cycle 2 it would be unacceptable or inadvisable to disturb the patient to carry out the activity.

Figure 19:
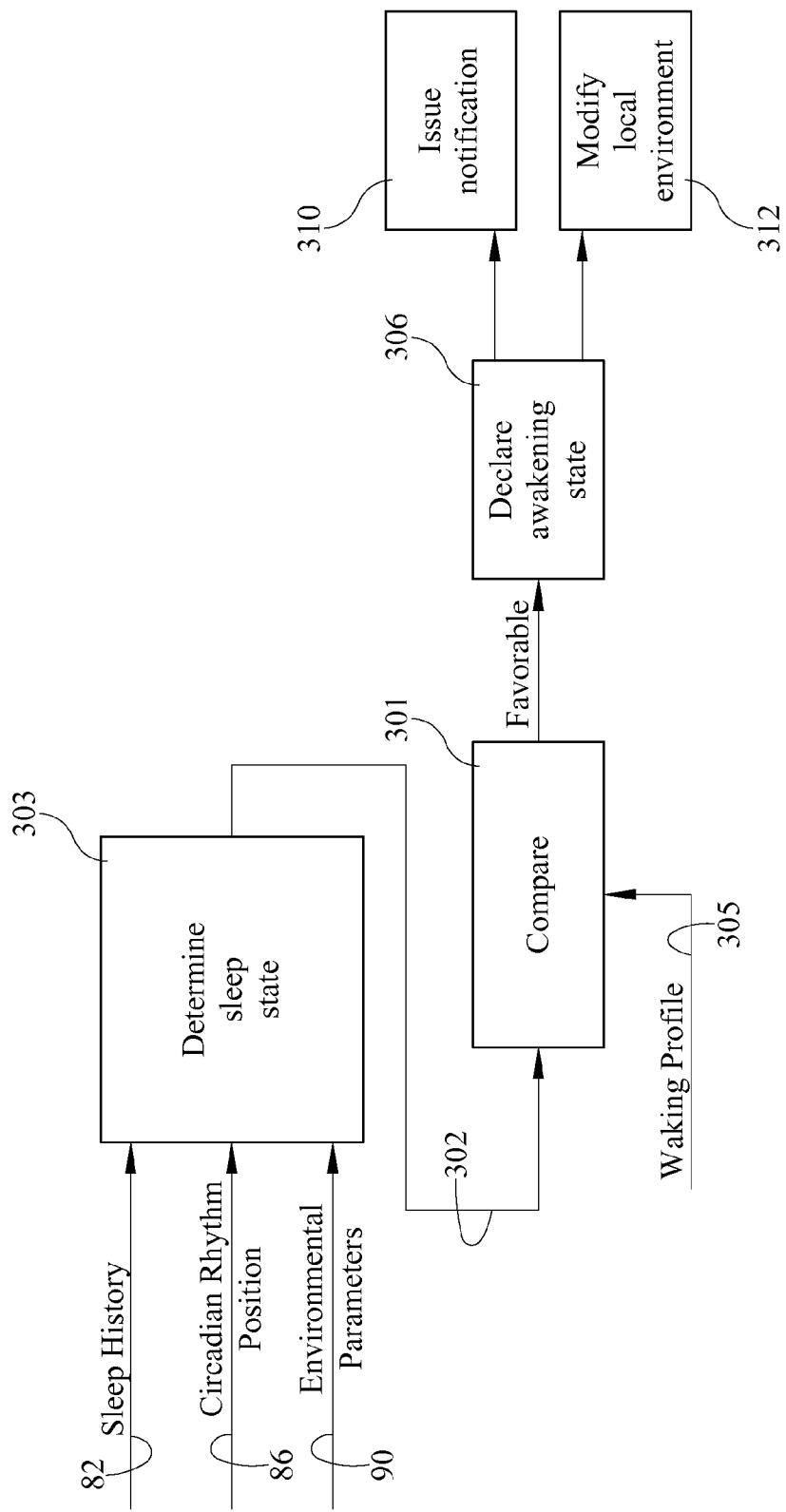
FIG. 19 is a block diagram according to this disclosure.

Referring to FIG. 19, a method of responding to awakening 302 of a person comprises comparing 301 the person's sleep state 303 to a waking profile 305; and if the sleep state 303 compares favorably to the profile 305, declaring 306 that the person is in an awakening state 302. In the method, the waking profile 305 is one of a) a person specific profile; b) a class specific profile; and c) a generic profile. In the method, the person's sleep state 303 is determined as a function of sleep history 82, circadian rhythm position 86 and at least one environmental parameter 90. In the method, if the person is declared 306 to be in the awakening state 302 the method comprises at least one of: a) issuing a notification 310; and b) modifying a local environment 312 to place the environment in a condition more compatible with the needs of an awakening person. In the method, issuing a notification 310 comprises one or more of activating a nurse call system; conveying a notice to a central location; and illuminating an indicator light; and modifying a local environment 312 comprises increasing ambient lighting intensity.

The system parameters such the segmentation of the TREM stage into substages, duration dependent and duration independent sleep values, desired time spent at each sleep stage or substage, unadjusted thresholds, values for the benefit and sleep disruptive potential of candidate activities, and the relationship between those values and a scale factor are based on any satisfactory source of information. These include caregiver experience and judgment and clinical studies. The parameters can be preestablished or may be left to caregiver discretion depending on factors such as tradeoffs involving caregiver workload and uniformity of care from patient to patient. The parameters can be highly patient specific, specific to different classes of patients based on factors such as gender, age, and medical condition (e.g. pre-operative, post operative, disoriented). Alternatively the parameter values can be facility-wide, patient independent values.

Although this disclosure refers to specific embodiments, it will be understood by those skilled in the art that various changes in form and detail may be made without departing from the subject matter set forth in the accompanying claims.

I claim:

1. A method for governing care of a person, the method comprising:

determining, with a decision engine, the importance of a candidate activity relative to the importance of patient sleep continuity; and if the candidate activity is more important than sleep continuity, carrying out the activity or indicating the acceptability of carrying out the activity; and if the candidate activity is not more important than sleep continuity, refraining from carrying out the activity or indicating that the unacceptability of carrying out the activity;

wherein the step of determining relative importance, with the decision engine, is a function of determining whether or not a sleep threshold value has been achieved and determining whether or not the candidate activity is considered unlikely to disrupt the patient's existing or upcoming sleep state, wherein if the step of determining relative importance determines that the candidate activity is not more important than sleep continuity, making the step of refraining block conditional on first determining that an alternate activity having a sleep disruptive potential lower than that of the candidate activity exists, redesignating the alternate activity as the candidate activity, repeating the step of determining relative importance and determining, with the decision engine, at that step that the redesignated activity is not more important than sleep continuity.

2. The method of claim 1 wherein the sleep threshold is a constant for any given candidate activity.

3. The method of claim 2 wherein the threshold is adjustable as a function of the importance and sleep disruptive potential of the given candidate activity.

4. The method of claim 1 wherein the sleep threshold is a nonconstant for any given candidate activity.

5. The method of claim 4 wherein the threshold is adjustable as a function of the importance and sleep disruptive potential of the given candidate activity.

6. A method for governing care of a person, the method comprising:

determining, with a decision engine, the importance of a candidate activity relative to the importance of patient sleep continuity; and if the candidate activity is more important than sleep continuity, carrying out the activity or indicating the acceptability of carrying out the activity; and if the candidate activity is not more important than sleep continuity, refraining from carrying out the activity or indicating that the unacceptability of carrying out the activity wherein the step of determining relative importance, with the decision engine, is a function of determining whether or not a sleep threshold value has been achieved and determining whether or not the candidate activity is considered unlikely to disrupt the patient's existing or upcoming sleep state, wherein if the step of determining relative importance, with the decision engine, determines that the candidate activity is not more important than sleep continuity, making the refraining step conditional on first determining that an alternate activity having a sleep disruptive potential lower than that of the candidate activity exists, redesignating the alternate activity as the candidate activity, repeating the step of determining whether or not the candidate activity is considered unlikely to disrupt the patient's existing or upcoming sleep state step and determining at that step that the activity is not unlikely to disrupt the patient's sleep, and repeating the step of determining relative importance and determining at that step that the redesignated activity is not more important than sleep continuity.

7. The method of claim 6 wherein the sleep threshold is a nonconstant target for any given candidate activity.

8. The method of claim 7 wherein the threshold is adjustable as a function of the importance and sleep disruptive potential of the given candidate activity.

9. A method for governing care of a person, the method comprising:
   determining, with a decision engine, if a sleep threshold has been achieved; and
   if the threshold has been achieved, carrying out a candidate activity or indicating the acceptability of carrying out the activity; and
   if the threshold has not been achieved determining, with the decision engine, if the candidate activity is unlikely to disturb the patient's current or upcoming sleep: and
   if the candidate activity is unlikely to disturb the patient's current or upcoming sleep, carrying out the candidate activity or indicating the acceptability of carrying out the activity: and
   if the candidate activity is not unlikely to disturb the patient's current or upcoming sleep, determining, with the decision engine, if the importance of carrying out the activity exceeds the importance of sleep continuity and
   if the importance of carrying out the activity exceeds the importance of sleep continuity, caring out the candidate activity or indicating the acceptability of carrying out the activity:
   wherein if the importance of carrying out the activity does not exceed the importance of sleep continuity refraining from carrying out the activity or indicating that the unacceptability of carrying out the activity.

10. The method of claim 9 wherein the sleep threshold is a constant target for any given candidate activity.

11. The method of claim 10 wherein the threshold is adjustable as a function of the importance and sleep disruptive potential of the given candidate activity.

12. The method of claim 9 wherein the activity is one of:
   a) operating a microclimate control system in a given mode of microclimate control operation;
   b) operating a sequential compression device in a given mode of sequential compression operation;
   c) operating a continuous lateral rotation therapy (CLRT) program in a given mode;
   d) operating a percussive function;
   e) conducting a patient condition assessment;
   f) repositioning the patient;
   g) attending to the patient's activities of daily living;
   h) administering a medication to the patient;
   i) housekeeping;
   j) facility maintenance;
   k) enabling or disabling telephone service;
   l) illuminating or extinguishing a sign;
   m) enabling or disabling a speaker; and
   n) controlling ambient lighting.

13. A method for governing care of a person, the method comprising:
   determining, with a decision engine, if a sleep threshold has been achieved; and
   if the threshold has been achieved, carrying out a candidate activity or indicating the acceptability of carrying out the activity; and
   if the threshold has not been achieved determining, with the decision engine, if the candidate activity is unlikely to disturb the patient's current or upcoming sleep; and
   if the candidate activity is unlikely to disturb the patient's current or upcoming sleep, carrying out the candidate activity or indicating the acceptability of carrying out the activity; and
   if the candidate activity is not unlikely to disturb the patient's current or upcoming sleep, determining, with the decision engine, if the importance of carrying out the activity exceeds the importance of sleep continuity; and
   if the importance of carrying out the activity exceeds the importance of sleep continuity, carrying out the candidate activity or indicating the acceptability of carrying out the activity:
   wherein if the importance of carrying out the activity does not exceed the importance of sleep continuity, determining, with the decision engine, if an alternate activity with a lower likelihood of disturbing sleep is available and, if such an activity exists,
   redesignating the alternate activity as the candidate activity and repeating the portion of the method beginning with the step of determining if the importance of carrying out the activity exceeds the importance of sleep continuity.

14. The method of claim 13 wherein the sleep threshold is a constant target for any given candidate activity.

15. The method of claim 14 wherein the threshold is adjustable as a function of the importance and sleep disruptive potential of the given candidate activity.

16. The method of claim 13 wherein the activity is one of:
   a) operating a microclimate control system in a given mode of microclimate control operation;
   b) operating a sequential compression device in a given mode of sequential compression operation;
   c) operating a continuous lateral rotation therapy (CLRT) program in a given mode;
   d) operating a percussive function;
   e) conducting a patient condition assessment;
   f) repositioning the patient;
   g) attending to the patient's activities of daily living;
   h) administering a medication to the patient;
   i) housekeeping;
   j) facility maintenance;
   k) enabling or disabling telephone service;
   l) illuminating or extinguishing a sign;
   m) enabling or disabling a speaker; and
   n) controlling ambient lighting.

17. A method for governing care of a person, the method comprising:
   determining, with a decision engine, if a sleep threshold has been achieved: and
   if the threshold has been achieved, carrying out a candidate activity or indicating the acceptability of carrying out the activity; and
   if the threshold has not been achieved determining, with the decision engine, if the candidate activity is unlikely to disturb the patient's current or upcoming sleep; and
   if the candidate activity is unlikely to disturb the patient's current or upcoming sleep, carrying out the candidate activity or indicating the acceptability of carrying out the activity; and
   if the candidate activity is not unlikely to disturb the patient's current or upcoming sleep, determining, with the decision engine, if the importance of carrying out the activity exceeds the importance of sleep continuity; and
   if the importance of carrying out the activity exceeds the importance of sleep continuity, carrying out the candidate activity or indicating the acceptability of carrying out the activity;

wherein if the importance of carrying out the activity does not exceed the importance of sleep continuity, determining if an alternate activity with a lower likelihood of disturbing sleep is available and, if such an activity exists,
redesignating the alternate activity as the candidate activity and repeating the portion of the method beginning with the step of determining if the candidate activity is unlikely to disturb the patient's current or upcoming sleep.

18. The method of claim 17 wherein the sleep threshold is a constant target for any given candidate activity.

19. The method of claim 18 wherein the threshold is adjustable as a function of the importance and sleep disruptive potential of the given candidate activity.

20. The method of claim 17 wherein the activity is one of:
   a) operating a microclimate control system in a given mode of microclimate control operation;
   b) operating a sequential compression device in a given mode of sequential compression operation;
   c) operating a continuous lateral rotation therapy (CLRT) program in a given mode;
   d) operating a percussive function;
   e) conducting a patient condition assessment;
   f) repositioning the patient;
   g) attending to the patient's activities of daily living;
   h) administering a medication to the patient;
   i) housekeeping;
   j) facility maintenance;
   k) enabling or disabling telephone service;
   l) illuminating or extinguishing a sign;
   m) enabling or disabling a speaker; and
   n) controlling ambient lighting.

21. A method for governing care of a person, the method comprising:
   determining, with a decision engine, if a sleep threshold has been achieved and
   if the threshold has been achieved, carrying out a candidate activity or indicating the acceptability of carrying out the activity; and
   if the threshold has not been achieved determining, with the decision engine, if the candidate activity is unlikely to disturb the patient's current or upcoming sleep; and
   if the candidate activity is unlikely to disturb the patient's current or upcoming sleep, carrying out the candidate activity or indicating the acceptability of carrying out the activity: and
   if the candidate activity is not unlikely to disturb the patient's current or upcoming sleep, determining, with the decision engine, if the importance of carrying out the activity exceeds the importance of sleep continuity; and
   if the importance of carrying out the activity exceeds the importance of sleep continuity, carrying out the candidate activity or indicating the acceptability of carrying out the activity:
   wherein if the importance of carrying out the activity does not exceed the importance of sleep continuity, determining, with the decision engine, if an alternate activity with a lower likelihood of disturbing sleep is available and if such an activity exists, carrying out the activity.

22. The method of claim 21 wherein the sleep threshold is a constant target for any given candidate activity.

23. The method of claim 22 wherein the threshold is adjustable as a function of the importance and sleep disruptive potential of the given candidate activity.

24. The method of claim 21 wherein the activity is one of:
   a) operating a microclimate control system in a given mode of microclimate control operation;
   b) operating a sequential compression device in a given mode of sequential compression operation;
   c) operating a continuous lateral rotation therapy (CLRT) program in a given mode;
   d) operating a percussive function;
   e) conducting a patient condition assessment;
   f) repositioning the patient;
   g) attending to the patient's activities of daily living;
   h) administering a medication to the patient;
   i) housekeeping;
   j) facility maintenance;
   k) enabling or disabling telephone service;
   l) illuminating or extinguishing a sign;
   m) enabling or disabling a speaker; and
   n) controlling ambient lighting.

25. A method for governing care of a person, the method comprising:
   determining, with a decision engine, the importance of a candidate activity relative to the importance of patient sleep continuity; and
   if the candidate activity is more important than sleep continuity, carrying out the activity or indicating the acceptability of carrying out the activity; and
   if the candidate activity is not more important than sleep continuity, refraining from carrying out the activity or indicating that the unacceptability of carrying out the activity:
   wherein the activity is one of:
   a) operating a microclimate control system in a given mode of microclimate control operation:
   b) operating a sequential compression device in a given mode of sequential compression operation;
   c) operating a continuous lateral rotation therapy (CLRT) program in a given mode;
   d) operating a percussive function;
   e) conducting a patient condition assessment;
   f) repositioning the patient;
   g) attending to the patient's activities of daily living;
   h) administering a medication to the patient;
   i) housekeeping;
   j) facility maintenance;
   k) enabling or disabling telephone service;
   l) illuminating or extinguishing a sign;
   m) enabling or disabling a speaker; and
   n) controlling ambient lighting;
   wherein: the given mode of microclimate control operation is one of:
   a) a mode for maintaining patient skin temperature at or below 98 degrees F. and
   b) a mode for maintaining patient skin temperature at or below 96 degrees F.; the given mode of sequential compression operation is one of:
   a) a first cyclic mode having a first frequency and a first amplitude;
   b) a second cyclic mode having a second frequency smaller than the first frequency and a second amplitude smaller than the first amplitude; and
   c) a constant compression mode;
   the patient condition assessment is one of a pain assessment and a skin condition assessment;
   the repositioning activity comprises turning the patient laterally; and
   the attending activity comprises one of bathing, feeding and toilet assistance.

26. A method for governing care of a person, the method comprising:

determining if a sleep threshold has been achieved; and if the threshold has been achieved, carrying out a candidate activity or indicating the acceptability of carrying out the activity; and if the threshold has not been achieved determining if the candidate activity is unlikely to disturb the patient's current or upcoming sleep; and if the candidate activity is unlikely to disturb the patient's current or upcoming sleep, carrying out the candidate activity or indicating the acceptability of carrying out the activity; and if the candidate activity is not unlikely to disturb the patient's current or upcoming sleep, determining if the importance of carrying out the activity exceeds the importance of sleep continuity; and if the importance of carrying out the activity exceeds the importance of sleep continuity, carrying out the candidate activity or indicating the acceptability of carrying out the activity;

wherein the activity is one of:
a) operating a microclimate control system in a given mode of microclimate control operation;
b) operating a sequential compression device in a given mode of sequential compression operation;
c) operating a continuous lateral rotation therapy (CLRT) program in a given mode;
d) operating a percussive function;
e) conducting a patient condition assessment;
f) repositioning the patient;
g) attending to the patient's activities of daily living;
h) administering a medication to the patient;
i) housekeeping;
j) facility maintenance;
k) enabling or disabling telephone service;
l) illuminating or extinguishing a sign;
m) enabling or disabling a speaker; and
n) controlling ambient lighting;

wherein:

the given mode of microclimate control operation is one of:
a) a mode for maintaining patient skin temperature at or below 98 degrees F. and
b) a mode for maintaining patient skin temperature at or below 96 degrees F.;

the given mode of sequential compression operation is one of:
a) a first cyclic mode having a first frequency and a first amplitude;
b) a second cyclic mode having a second frequency smaller than the first frequency and a second amplitude smaller than the first amplitude; and
c) a constant compression mode;

the patient condition assessment is one of a pain assessment and a skin condition assessment;

the repositioning activity comprises turning the patient laterally; and the attending activity comprises one of bathing, feeding and toilet assistance.

* * * * *

UNITED STATES PATENT AND TRADEMARK OFFICE
CERTIFICATE OF CORRECTION

Page 1 of 1

PATENT NO. : 9,152,768 B2
APPLICATION NO. : 13/245378
DATED : October 6, 2015
INVENTOR(S) : Ribble It is certified that error appears in the above-identified patent and that said Letters Patent is hereby corrected as shown below:

In the claims

Claim 25, Col. 14, line 40, replacing "activity:" with --activity;--

Claim 25, Col. 14, line 33, replacing "operator:" with --operator;--

Signed and Sealed this
Nineteenth Day of April, 2016

Michelle K. Lee
*Director of the United States Patent and Trademark Office*